US 12,254,536 B2

United States Patent
Takeshima

(10) Patent No.: US 12,254,536 B2
(45) Date of Patent: Mar. 18, 2025

(54) RECONSTRUCTION APPARATUS, METHOD, AND PROGRAM

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 288 days.

(21) Appl. No.: 17/660,233

(22) Filed: Apr. 22, 2022

(65) Prior Publication Data
US 2022/0343565 A1     Oct. 27, 2022

(30) Foreign Application Priority Data

Apr. 26, 2021 (JP) .................................. 2021-074226
Apr. 19, 2022 (JP) .................................. 2022-068935

(51) Int. Cl.
| G06T 11/00 | (2006.01) |
| G06T 5/70 | (2024.01) |
| G16H 50/20 | (2018.01) |

(52) U.S. Cl.
CPC .............. *G06T 11/005* (2013.01); *G06T 5/70* (2024.01); *G16H 50/20* (2018.01)

(58) Field of Classification Search
CPC .......... G06T 11/005; G06T 5/70; G16H 50/20
See application file for complete search history.

(56) References Cited

U.S. PATENT DOCUMENTS

| 6,249,595 B1 * | 6/2001 | Foxall ................... G06T 11/006 382/128 |
| 10,156,624 B2 * | 12/2018 | Paul .................... G01R 33/4828 |
| 2011/0150305 A1 * | 6/2011 | Zeng ..................... G06T 11/005 382/131 |
| 2013/0051674 A1 * | 2/2013 | Goossens ................. G06T 5/10 382/173 |
| 2015/0086097 A1 * | 3/2015 | Chen .................... G06T 11/006 382/131 |
| 2015/0137811 A1 * | 5/2015 | Muftuler ............... G06T 11/008 324/309 |

(Continued)

OTHER PUBLICATIONS

Bao, Yufang, and Andrew A. Maudsley. "Improved reconstruction for MR spectroscopic imaging." IEEE transactions on medical imaging 26.5 (2007): 686-695. (Year: 2007).*

(Continued)

*Primary Examiner* — Utpal D Shah
(74) *Attorney, Agent, or Firm* — Oblon, McClelland, Maier & Neustadt, L.L.P.

(57) ABSTRACT

According to one embodiment, a reconstruction apparatus obtains acquired raw data, and reconstruct a data set that represents a measured physical amount with a multidimensional space based on the acquired raw data. Herein, the apparatus performs reduction processing for generating noise-reduced partial data from partial data relating to a partial area of a data set at a current number of iterations, error compensation processing for compensating errors in a data set at the current number of iterations with respect to the acquired raw data, and optimization processing for reconstructing the data set by repeating the reduction processing and the error compensation processing until predetermined criteria are met, while moving the partial area.

14 Claims, 12 Drawing Sheets

(56) References Cited

U.S. PATENT DOCUMENTS

| | | | | |
|---|---|---|---|---|
| 2015/0279065 | A1* | 10/2015 | Li | G01R 33/561 |
| | | | | 382/131 |
| 2015/0348288 | A1* | 12/2015 | Hagiwara | G06T 11/003 |
| | | | | 382/131 |
| 2018/0174335 | A1* | 6/2018 | Yamakawa | G06T 5/70 |
| 2019/0336095 | A1* | 11/2019 | Ritter | G06T 7/11 |
| 2020/0355772 | A1* | 11/2020 | Eggers | G01R 33/56554 |
| 2021/0364589 | A1* | 11/2021 | Bilgic | A61B 5/7207 |
| 2023/0421746 | A1* | 12/2023 | Cao | H04N 13/282 |
| 2024/0185485 | A1* | 6/2024 | Salomon | G06T 11/006 |

OTHER PUBLICATIONS

Jhamb, Tanuj Kumar, Vinith Rejathalal, and V. K. Govindan. "A review on image reconstruction through MRI k-space data." International journal of image, graphics and signal processing 7.7 (2015): 42. (Year: 2015).*

Lam, F. et al. "A Subspace Approach to High-Resolution Spectroscopic Imaging", Magnetic Resonance in Medicine 71:1349-1357, 2014. 9 pages.

* cited by examiner

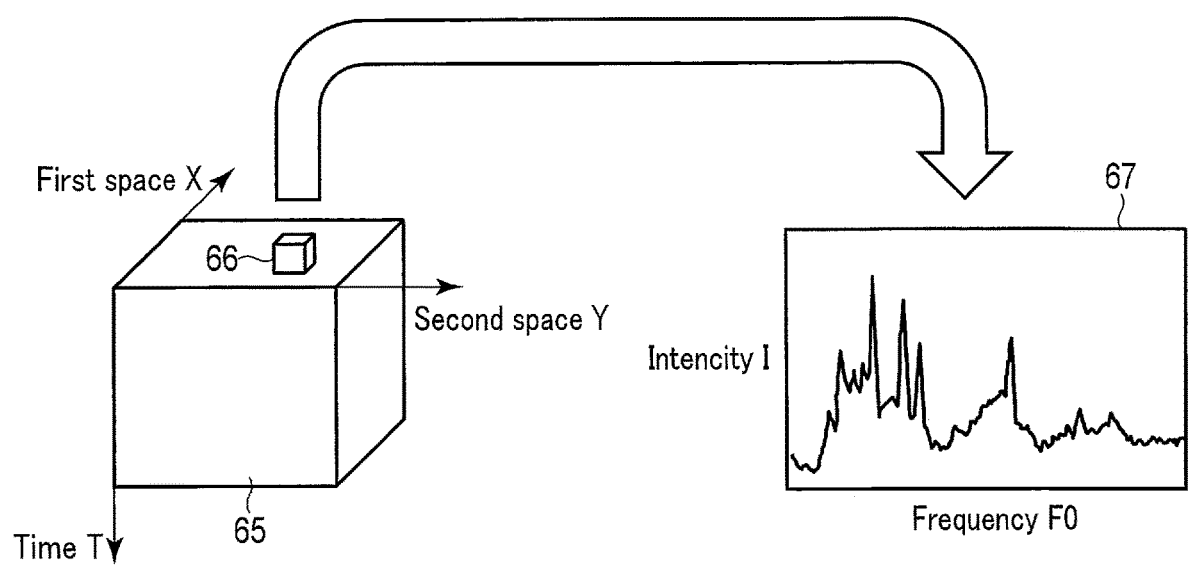
F I G. 4

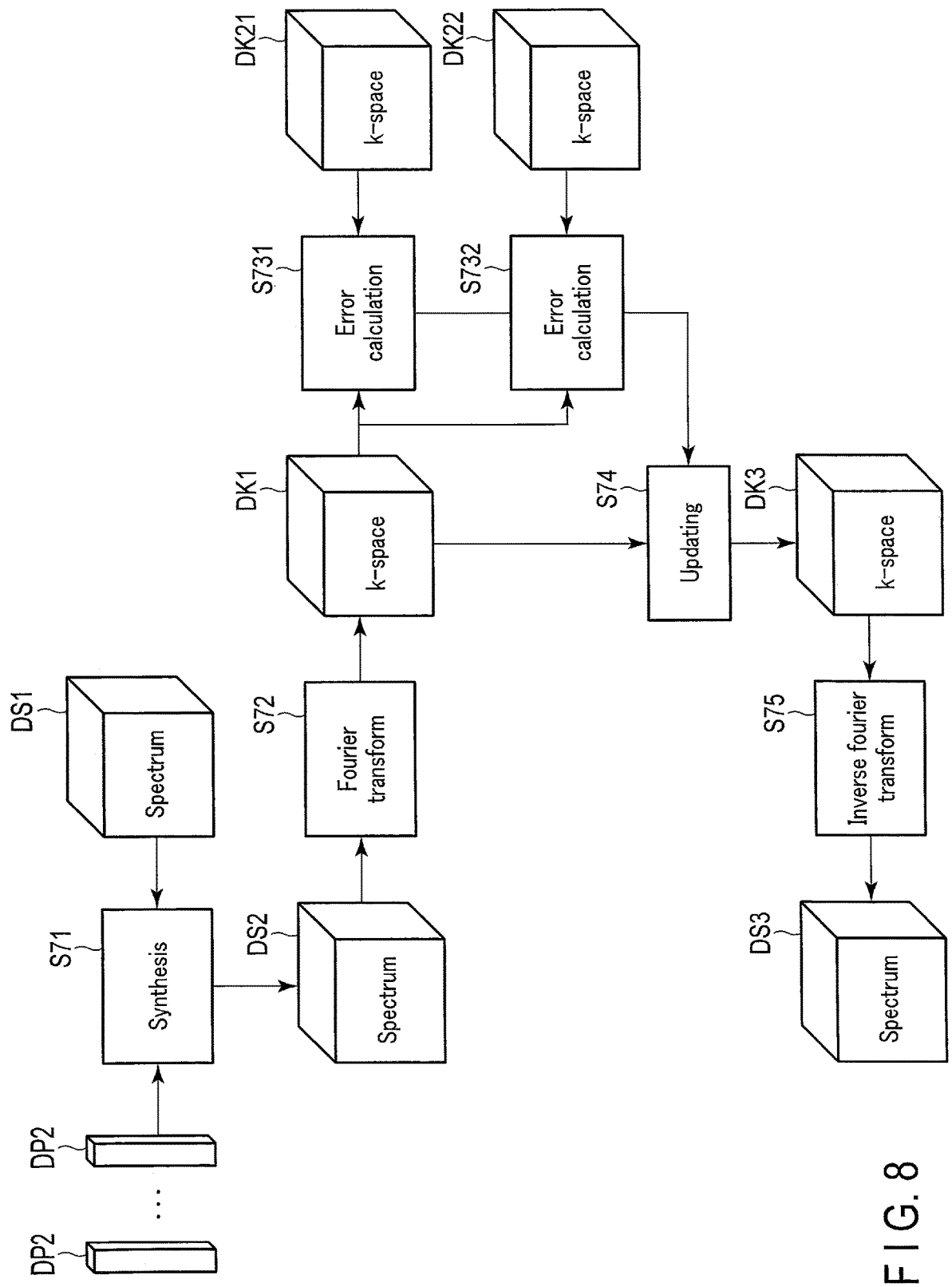
F I G. 8

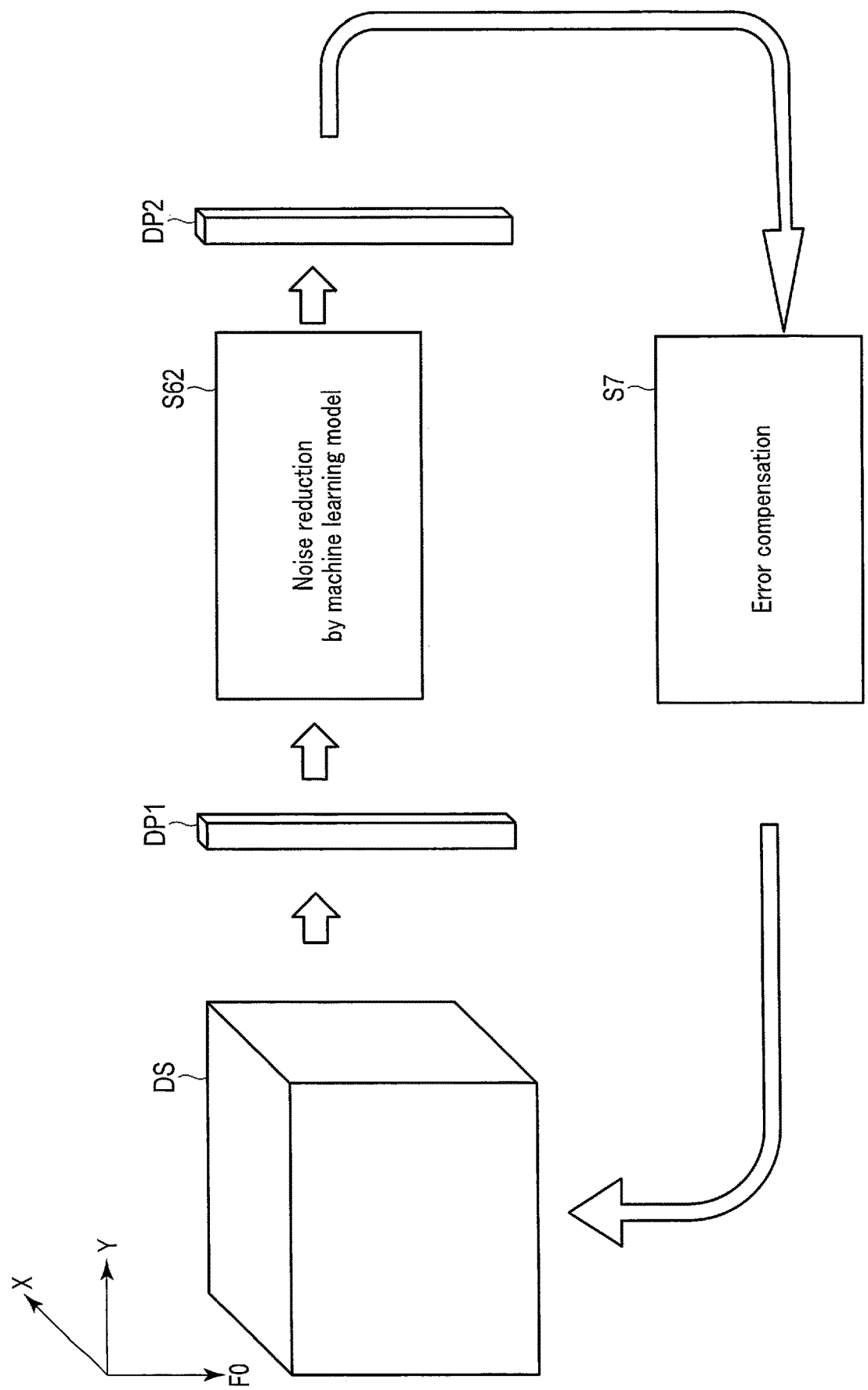
F I G. 9

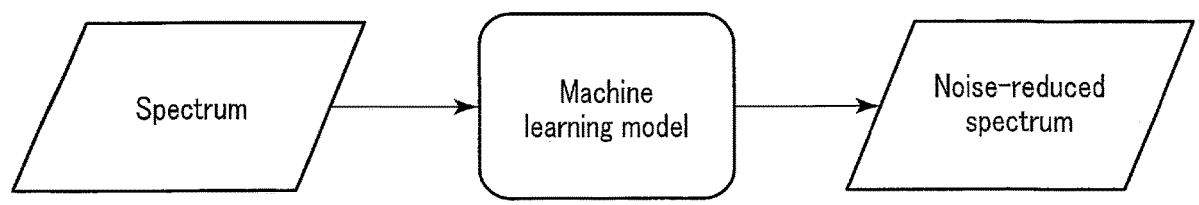
F I G. 10

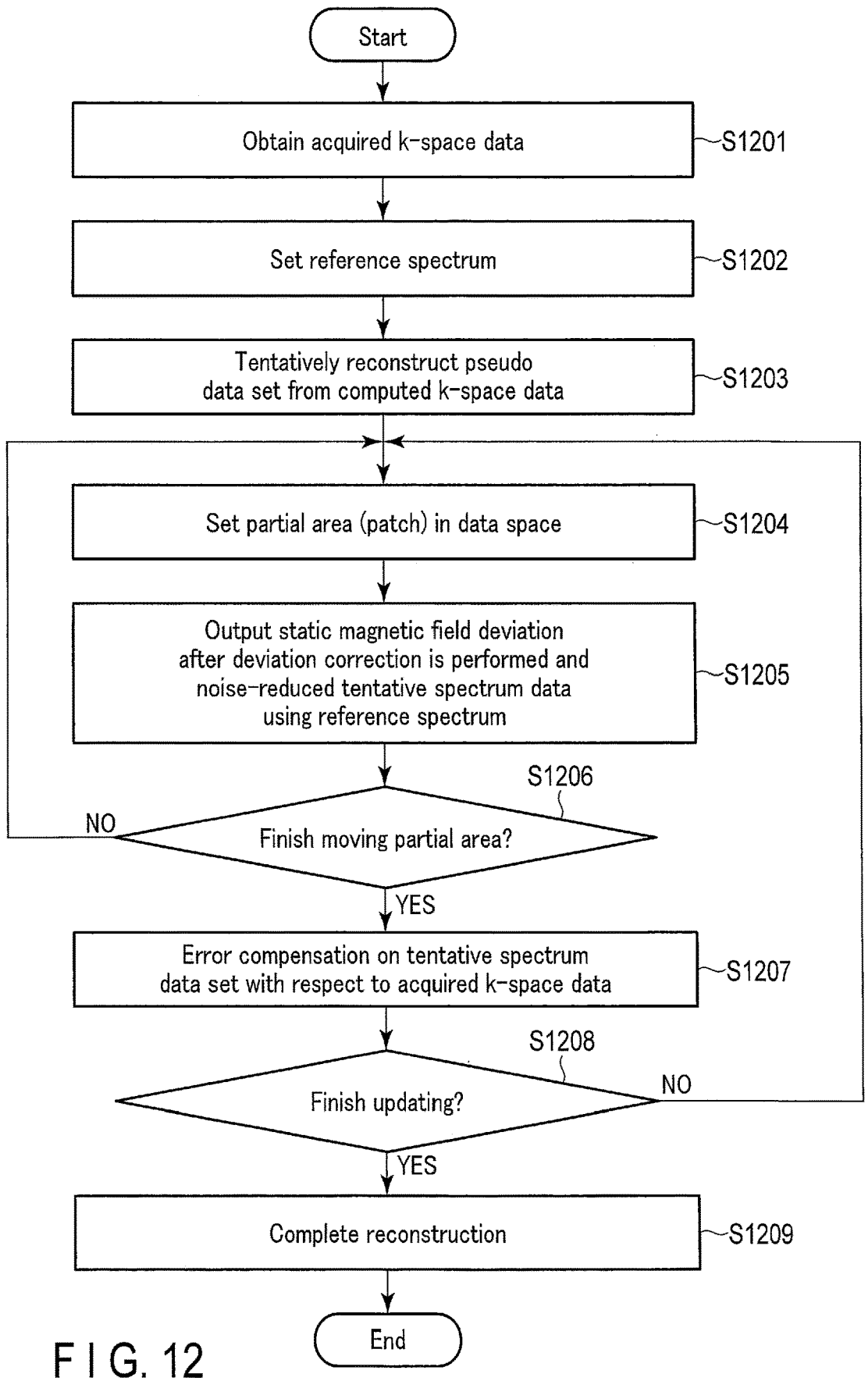
F I G. 12

RECONSTRUCTION APPARATUS, METHOD, AND PROGRAM

CROSS-REFERENCE TO RELATED APPLICATIONS

This application is based upon and claims the benefit of priority from prior Japanese Patent Application No. 2021-074226, filed Apr. 26, 2021; and No. 2022-068935, filed Apr. 19, 2022; the entire contents of all of which are incorporated herein by reference.

FIELD

Embodiments disclosed herein relate generally to a reconstruction apparatus, method, and program.

BACKGROUND

Chemical shift imaging is an example of a method of measuring chemical shift frequencies, which are a minute difference between resonance frequencies caused by differences in a chemical environment. For each voxel included in a field of view (FOV), a spectrum that represents a frequency in a horizontal axis and a signal intensity in a vertical axis is reconstructed based on k-space data collected by chemical shift imaging. A frequency corresponding to each peak of a spectrum represents a chemical shift frequency of a molecule. Since a resonance frequency changes in accordance with a static magnetic field, spatial or temporal non-uniformity of a static magnetic field is one of the factors that degrade the accuracy of a spectrum to be reconstructed.

BRIEF DESCRIPTION OF THE DRAWINGS

FIG. 4 is a diagram schematically showing a spectrum data set.

FIG. 8 is a diagram schematically showing a flow of an example of a second type of error compensation processing.

FIG. 9 is a diagram schematically showing a processing example of steps S4 to S9 in FIG. 5 (noise reduction by a machine learning model).

FIG. 10 is a diagram showing an example of an input and an output of a machine learning model.

FIG. 12 is a diagram showing a flow of an example of another reconstruction of a spectrum data set.

DETAILED DESCRIPTION

A reconstruction apparatus according to an embodiment includes processing circuitry. The processing circuitry obtains acquired raw data acquired by a medical image diagnosis apparatus, and reconstruct, based on the acquired raw data, a data set that represents a measured physical amount with a multidimensional space defined by a space axis, a time axis, and a component axis. Herein, the processing circuitry performs reduction processing, error compensation processing, and optimization processing. By the reduction processing, the processing circuitry generates a second partial data from a first partial data relating to a partial area in a data set at the current number of iterations. By the error compensation processing, the processing circuitry compensates errors of the data set at the current number of iterations with respect to the acquired raw data. By the optimization processing, the processing circuitry reconstructs the data set by repeating the reduction processing and the error processing until predetermined criteria are met, while moving the partial area.

Embodiments of a reconstruction apparatus, method, and program will be described in detail below with reference to the accompanying drawings.

Figure 1:
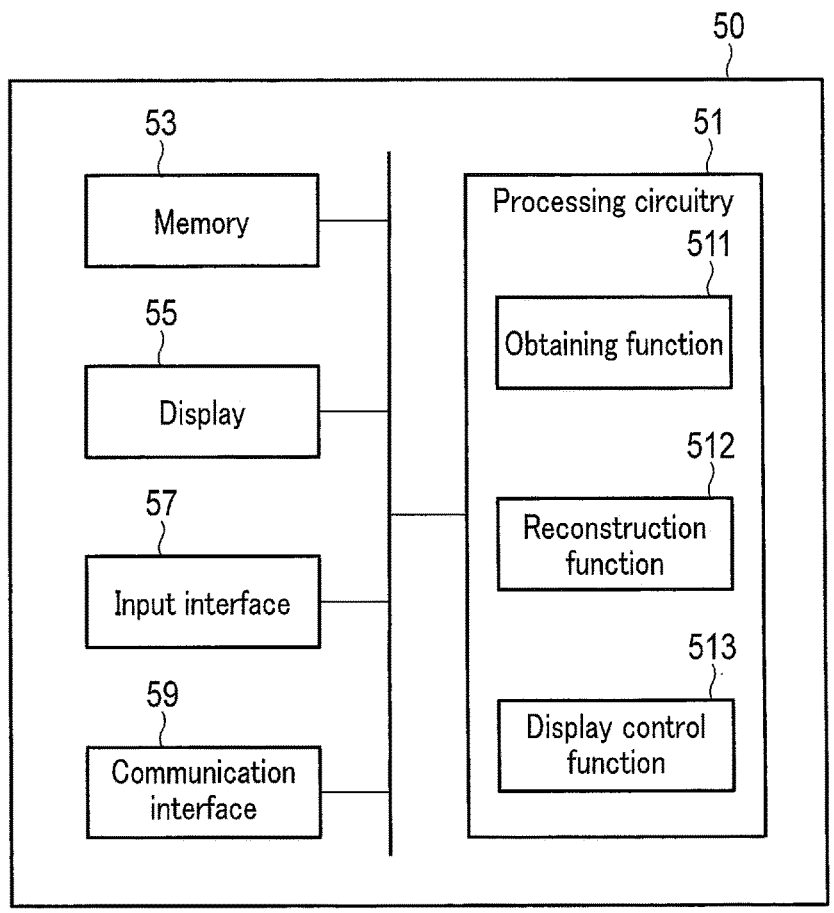
FIG. 1 is a diagram showing a configuration example of a reconstruction apparatus.

FIG. 1 is a diagram showing a configuration example of a reconstruction apparatus 50 according to the present embodiment. The reconstruction apparatus 50 according to the present embodiment is a computer having processing circuitry 51, a memory 53, a display 55, an input interface 57, and a communication interface 59. Data communications between the processing circuitry 51, the memory 53, the display 55, the input interface 57, and the communication interface 59 are performed via a bus, for example.

The processing circuitry 51 includes a processor such as a CPU, etc. as hardware resources. The processing circuitry 51 functions as the main unit of the reconstruction apparatus 50. For example, the processing circuitry 51 executes a reconstruction program to implement an obtainment function 511, a reconstruction function 512, and a display control function 513. The reconstruction program is stored in a non-transitory storage medium, such as the memory 53, etc. The reconstruction program is read by the processing circuitry 51, and the processing circuitry 51 loads the read reconstruction program into the memory 53, etc. and executes it to implement the obtainment function 511, the reconstruction function 512, and the display control function 513. The reconstruction program may be managed as a single file and may be divided into multiple modules in accordance with types of function, etc.

Through implementation of the obtainment function 511, the processing circuitry 51 obtains raw data acquired by performing medical imaging on a subject. Raw data acquired by medical imaging will be referred to as "acquired raw data". Medical imaging is performed by a medical imaging diagnosis apparatus. As a medical image diagnostic apparatus according to the present embodiment, any type is applicable as long as raw data can be acquired by medical imaging performed on a subject in accordance with the principle of medical imaging for the selected medical image diagnosis apparatus. For example, a magnetic resonance imaging apparatus, an X-ray computed tomography apparatus, an X-ray diagnosis apparatus, an ultrasonic diagnostic apparatus, and a nuclear medicine diagnostic apparatus are applicable as the medical image diagnosis apparatus according to the present embodiment. As raw data, k-space data in a magnetic resonance imaging apparatus, projection data and sinogram data in an X-ray computed tomography apparatus, projection data in an X-ray diagnosis apparatus, B-mode data and Doppler-mode data in an ultrasonic diagnostic apparatus, and coincidence data and sinogram data in a nuclear medicine diagnostic apparatus can be used.

Through the implementation of the reconstruction function 512, the processing circuitry 51 reconstructs a data set that expresses a measured physical quantity in a multidimensional space defined by a space axis, a time axis, and a component axis. Specifically, the processing circuitry 51 performs reduction processing, error compensation processing, and optimization processing. In the reduction processing, the processing circuitry 51 generates, from first partial data relating to a partial area of a data set at the current number of iterations, second partial data in which noise is reduced. In the error compensation processing, the processing circuitry 51 compensates an error in a data set at the current number of iterations with respect to the acquired raw data. In the optimization processing, the processing circuitry 51 repeats the reduction processing and the error compensation processing as the partial area in the data space is changed until predetermined criteria are met, thereby reconstructing a data set. Hereinafter, a data set for which reconstruction is completed will be called a "reconstructed data set".

Figure 2:
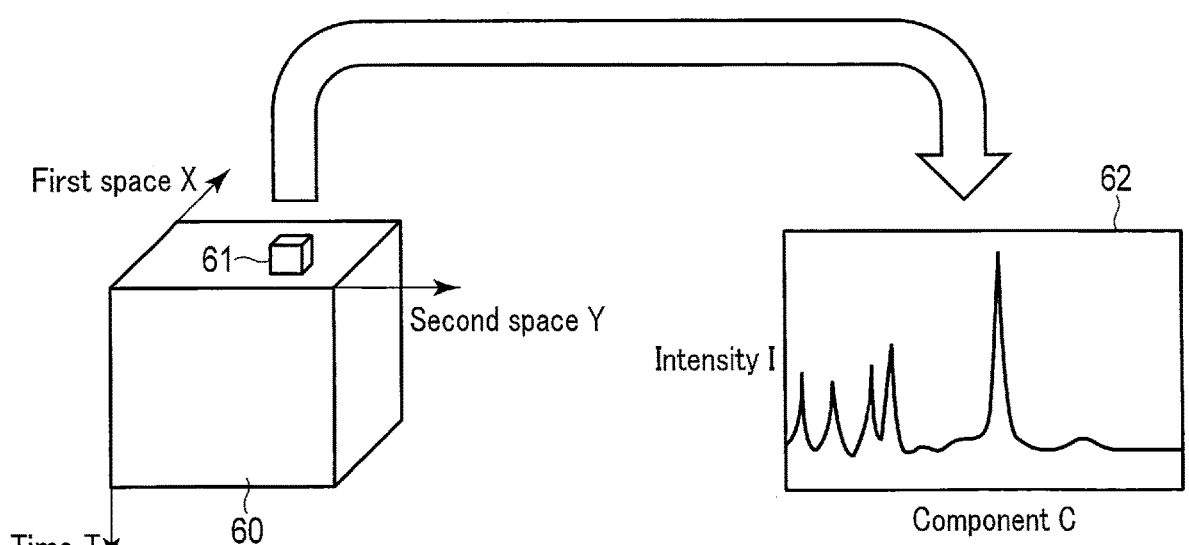
FIG. 2 is a diagram schematically showing a reconstructed data set.

FIG. 2 is a diagram schematically showing a reconstructed data set. As shown in FIG. 2, a reconstructed data set is a data set in which a measured physical quantity is allocated to each point in a multidimensional space. A multidimensional space has a space axis, a time axis, and a component axis. The space axis defines a location at which a physical quantity is measured. The time axis defines a time at which a measured physical quantity is acquired. The component axis defines a component representing a measured physical quantity. The data space 60 illustrated in FIG. 2 is defined by space axes and a time axis for easy understanding. The data space 60 may be expressed as a "temporal space". The data space 60 consists of a plurality of sample points 61. Each sample point 61 is assigned a measured physical quantity 62. The measured physical quantity 62 is expressed by an intensity axis relating to an intensity of the measured physical quantity and a component axis relating to a specific component included in the measured physical quantity. The specific component is a component that an operator focuses on among various components that characterize a measured physical quantity.

In FIG. 2, the number of dimensions of a spatial dimension of the data space 60 is two dimensions, consisting of a first space X and a second space Y. An intensity I of the measured physical quantity can be expressed by I=(X, Y, T, C) based on a first space X, a second space Y, a time T, and a component C. The number of dimensions of the space axis is not limited two; it may be one dimension or three dimensions. As a reconstructed data set, for example, a data set of reconstructed image data of a high tube voltage and reconstructed image data of a low tube voltage, which are acquired by dual energy scanning of the X-ray computed tomography apparatus, is applicable. In this case, a projection value or a CT value corresponds to the measured physical quantity, and a tube voltage corresponds to the above-mentioned specific component. As another example of a reconstructed data set, a data set that includes reconstructed image data of a plurality of energy bandwidths acquired by fluorescent photon counting scanning of the X-ray computed tomography apparatus may be applied. In this case, the number of photons or a CT value corresponds to the measured physical quantity, and an energy band width corresponds to the above-mentioned specific component.

Through the implementation of the display control function 513, the processing circuitry 51 displays various types of information on the display 55. For example, the processing circuitry 51 displays a reconstructed data set and the like on the display 55.

The memory 53 is a storage device, such as a hard disk drive (HDD), a solid state drive (SSD), or an integrated circuit storage device, which stores various types of information. The memory 53 may be a drive that reads and writes various types of information from and in a portable storage medium such as a CD-ROM drive, a DVD drive, or a flash memory. For example, the memory 53 stores a reconstruction program, acquired raw data, and reconstructed data sets, etc.

Through the display control function 513, the display 55 displays various types of information. As the display 55, for example, a CRT display, a liquid crystal display, an organic EL display, an LED display, a plasma display, or any other display known in the relevant technical field may be used as appropriate.

The input interface 57 includes an input device that receives various commands from a user. Examples of the input apparatus that can be used include a keyboard, a mouse, various switches, a touch screen, a touch pad, and the like. It should be noted that the input apparatus is not limited to those having physical operation parts such as the mouse and the keyboard. The input interface 57 also includes, for example, electric signal processing circuitry that receives an electric signal corresponding to an input operation through an external input device provided separately from the reconstruction apparatus 50 and outputs the received electric signal to different circuitry. The input interface 57 may also be a voice recognition device which receives a voice signal acquired via a microphone and converts the voice signals into an instruction signal.

The communication interface 59 is an interface performing data communications with external apparatuses, such as a medical image diagnosis apparatus, a workstation, a picture archiving and communication system (PACS), a hospital information system (HIS), a radiology information system (RIS), or the like, via a local area network (LAN) or the like.

The reconstruction apparatus 50 is described specifically. In the following description, suppose that the reconstruction apparatus 50 is a computer incorporated into a magnetic resonance imaging apparatus.

Figure 3:
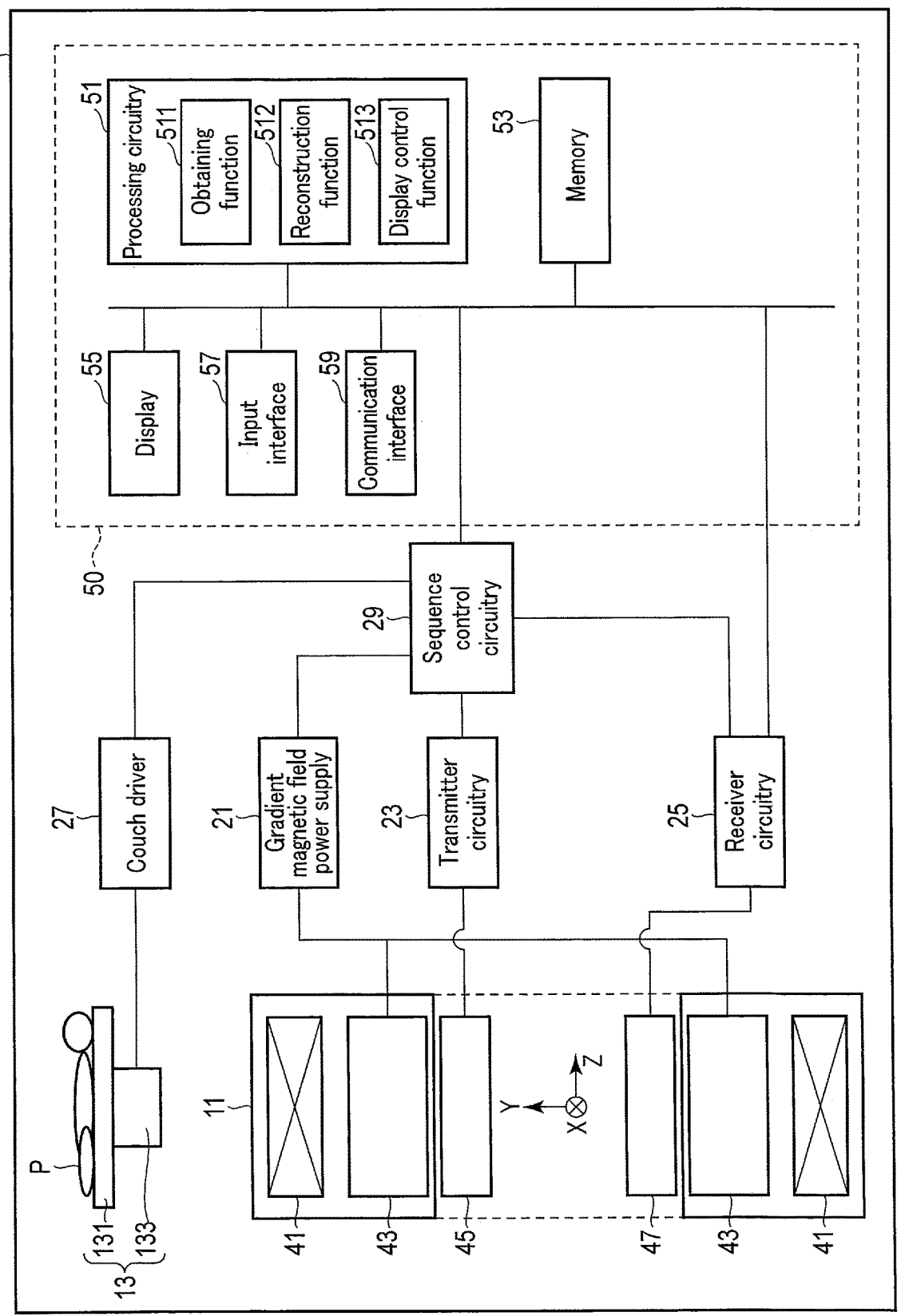
FIG. 3 is a diagram showing a configuration example of a magnetic resonance imaging apparatus.

FIG. 3 is a diagram showing a configuration example of the magnetic resonance imaging apparatus 1 according to the present embodiment. As shown in FIG. 3, the magnetic resonance imaging apparatus 1 includes a gantry 11, a couch 13, a gradient magnetic field power supply 21, transmitter circuitry 23, receiver circuitry 25, a couch driver 27, sequence control circuitry 29, and a reconstruction apparatus (host computer) 50.

The gantry 11 includes a static magnetic field magnet 41 and a gradient magnetic field coil 43. The static magnetic field magnet 41 and the gradient magnetic field coil 43 are accommodated in the housing of the gantry 11. A bore with a hollow shape is formed in the housing of the gantry 11. A transmitter coil 45 and a receiver coil 47 are disposed in the bore of the gantry 11.

The static magnetic field magnet 41 has a hollow approximately cylindrical shape and generates a static magnetic field inside the approximately cylindrical shape. The static magnetic field magnet 41 uses, for example, a permanent magnet, superconducting magnet, normal conducting magnet, etc. The central axis of the static magnetic field magnet 41 is defined as a Z-axis; an axis vertically perpendicular to the Z-axis is defined as a Y-axis; and an axis horizontally perpendicular to the Z-axis is defined as an X-axis. The X-axis, the Y-axis and the Z-axis constitute an orthogonal three-dimensional coordinate system.

The gradient magnetic field coil 43 is a coil unit attached to the inside of the static magnetic field magnet 41 and formed in a hollow approximately cylindrical shape. The gradient magnetic field coil 43 generates a gradient field upon receiving a current supplied from the gradient magnetic field power supply 21. Specifically, the gradient magnetic field coil 43 includes three coils corresponding respectively to the X, Y, and Z axes which are perpendicular to each other. The three coils generate gradient fields in which the magnetic field magnitude changes along the X, Y, and Z axes. The gradient magnetic fields along the X, Y, and Z axes are combined to generate a slice selective gradient field Gs, a phase encode gradient field Gp, and a frequency encode gradient field Gr, which are perpendicular to each other, in desired directions. The slice selective gradient magnetic field Gs is used to discretionarily determine an imaging slice. The phase encoding gradient magnetic field Gp is used to change a phase of magnetic resonance signals (hereinafter "MR signals") in accordance with a spatial position. The frequency encoding gradient magnetic field Gr is used to change a frequency of MR signals in accordance with a spatial position. In the following description, it is assumed that the gradient direction of the slice selective gradient magnetic field Gs aligns with the Z axis, the gradient direction of the phase encoding gradient magnetic field Gp aligns with the Y axis, and the gradient direction of the frequency encoding gradient field Gr aligns with the X axis.

The gradient magnetic field power supply 21 supplies a current to the gradient magnetic field coil 43 in accordance with a sequence control signal from the sequence control circuitry 29. Through the supply of the current to the gradient magnetic field coil 43, the gradient magnetic field power supply 21 makes the gradient magnetic field coil 43 generate gradient magnetic fields along the X-axis, the Y-axis, and the Z-axis. These gradient fields are superimposed on the static magnetic field formed by the static magnetic field magnet 41 and applied to the subject P.

The transmitter coil 45 is arranged inside the gradient magnetic field coil 43 and generates a high-frequency pulse (hereinafter referred to as an RF pulse) upon receiving a current supplied from the transmitter circuitry 23.

The transmitter circuitry 23 supplies a current to the transmitter coil 45 in order to apply an RF pulse for exciting a target proton in the subject P to the subject P via the transmitter coil 45. The RF magnetic field pulse vibrates at a resonance frequency specific to the target protons, and also electrically excites those target protons. An MR signal is generated from an electrically excited target proton and is detected by the receiver coil 47. The transmitter coil 45 is, for example, a whole-body coil (WB coil). The whole-body coil may be used as a transmitter/receiver coil.

The receiver coil 47 receives MR signals generated from the target protons in the subject P due to the effects of the RF pulse. The receiver coil 47 includes a plurality of receiver coil elements capable of receiving an MR signal. The received MR signal is supplied to the receiver circuitry 25 via wire or radio. Although not shown in FIG. 1, the receiver coil 47 has a plurality of reception channels arranged in parallel. Each receiver channel includes a receiver coil element which receives MR signals, an amplifier which amplifies the MR signals, etc. An MR signal is output from each reception channel. The total number of the reception channels may be equal to, larger than, or smaller than the total number of the receiver coil elements.

The receiver circuitry 25 receives an MR signal generated from the excited target proton via the receiver coil 47. The receiver circuitry 25 processes the received MR signal to generate a digital MR signal. The digital MR signal can be expressed by a k-space defined by spatial frequency. Thus, the digital MR signals are referred to as k-space data. The k-space data is an example of raw data. The k-space data is supplied to the reconstruction apparatus 50 either by wiring or wirelessly.

The transmitter coil 45 and the receiver coil 47 described above are merely examples. A transmitter/receiver coil which has a transmit function and a receive function may be used instead of the transmitter coil 45 and the receiver coil 47. Alternatively, the transmitter coil 45, the receiver coil 47, and the transmitter/receiver coil may be combined.

The couch 13 is installed adjacent to the gantry 11. The couch 13 includes a top plate 131 and a base 133. The subject P is placed on the top plate 131. The base 133 supports the top plate 131 slidably along each of the X-axis, the Y-axis, and the Z-axis. The couch driver 27 is accommodated in the base 133. The couch driver 27 moves the top plate 131 under the control of the sequence control circuitry 29. The couch driver 27 may include any type of motor such as a servo motor or stepping motor.

The sequence control circuitry 29 includes, as hardware resources, a processor such as a central processing unit (CPU) or a microprocessing unit (MPU), and a memory such as a read-only memory (ROM) or a random-access memory (RAM). The sequence control circuitry 29 controls the gradient magnetic field power supply 21, the transmitter circuitry 23, and the receiver circuitry 25 synchronously based on data collection conditions set by the processing circuitry 51, etc., and acquires k-space data relating to a subject P. The sequence control circuitry 29 is an example of the sequence control unit. The k space data acquired by data acquisition may be referred to as "acquired k-space data".

The sequence control circuitry 29 according to the present embodiment carries out data acquisition by MR spectroscopy, which is a type of chemical shift measurement. The chemical shift measurement is a technique of measuring a chemical shift, which is a minor difference in resonance frequency of a target proton such as a hydrogen nucleus, which is caused in accordance with a difference in chemical environment. The MR spectroscopy includes a single voxel method in which data acquisition is performed on a single voxel and a multi-voxel method in which data acquisition is performed on a plurality of voxels, and the present embodiment can be applied to either method. The multi-voxel method is also referred to as chemical shift imaging (CSI) or MRS imaging (MRSI). In the present embodiment, MR spectroscopy of a multi-voxel method may be referred to as chemical shift imaging or CSI.

The sequence control circuitry 29 performs CSI data acquisition on a subject P in accordance with conditions for preset data acquisition. Through performing of the CSI data acquisition, a free induction decay (FID) signal or a spin echo signal is generated from a measurement-target voxel of the subject P. The receiver circuitry 25 receives an FID signal or a spin echo signal via the receiver coil 47, and processes the received FID signal or spin echo signal to acquire k-space data relating to the measurement-target voxel. Let us assume that the acquired k-space data is digital data expressing, by a time function, the value of the intensity of the signal emitted from the measurement-target voxel. A pulse sequence of CSI is repeated for the number of excitations (NEX), and k-space data corresponding to the number of excitations is acquired.

The data acquisition conditions are automatically or manually set by the sequence control circuitry 29 or the processing circuitry 51, etc. Examples of the data acquisition conditions of CSI include a pulse sequence, a repetition time (TR), an echo time (TE), the number of excitations, a spectrum width, the number of times of sampling, a data acquisition method, and an area selection pulse, etc. As a pulse sequence, for example a PRESS (point resolved spectroscopy) method, a STEAM (stimulated echo acquisition mode) method, or applications of these methods may be used. As for a TR, a long TR is set at 5000 ms or longer, and a short TR is set between 1000 ms and 3000 ms, for example. As a TR becomes longer, an acquired MR signal intensity value approximates to a true value but a length of a data collection time increases. As for a TE, it is preferable that a long TE be set at 100 ms to 300 ms in this order and a short TE be set at 20 ms to 100 ms in this order. The shorter a TE is, the greater the increase in the number of peaks; the longer a TE is, the greater the decrease in the number of peaks.

The number of excitations is not particularly limited, and may be set to 1 or a larger value. A spectrum width and the number of times of sampling are condition items relating to a spectrum resolution. It suffices that the spectrum width and the number of times of sampling are set at discretionary values. As described above, the data acquisition method includes a single voxel method in which a spectrum of one voxel is obtained by one data acquisition, and a multi-voxel method in which spectra of a plurality of voxels are obtained by one data acquisition. The area selection pulse includes a pulse for exciting hydrogen nuclei in a limited set area, and a pulse for not exciting hydrogen nuclei in a limited set area. As the data acquisition condition, whether or not to apply the area selection pulse, frequency information on the selected area, and the like are set.

As shown in FIG. 3, the reconstruction apparatus 50 is a computer including processing circuitry 51, a memory 53, a display 55, an input interface 57, and a communication interface 59. The descriptions of the memory 53, the display 55, the input interface 57, and the communication interface 59 are omitted.

The processing circuitry 51 includes a processor such as a CPU, etc. as a hardware resource. The processing circuitry 51 functions as the main unit of the MRI apparatus 1. For example, the processing circuitry 51 executes various programs to implement an obtainment function 511, a reconstruction function 512, and a display control function 513.

Through the implementation of the obtainment function 511, the processing circuitry 51 obtains k-space data acquired through CSI performed by the sequence control circuitry 29. The processing circuitry 51 may obtain acquired k-space data directly from the sequence control circuitry 29 or the receiver circuitry 25 or temporarily stored acquired k-space data from the memory 53.

Through the implementation of the reconstruction function 512, the processing circuitry 51 reconstructs, based on the acquired raw data, a data set (reconstructed data set) that represents a signal intensity value in a multidimensional space consisting of a space axis, a time axis, and a chemical shift frequency axis. A frequency distribution of signal intensity values is called a spectrum. A reconstructed data set is a data set of spectra at respective points in a time space defined by a space axis and a time axis. In other words, the reconstructed data set is a spatial-temporal distribution of spectra. Hereinafter, such a reconstructed data set will be called a "spectrum data set". Specifically, the processing circuitry 51 performs reduction processing, error compensation processing, and optimization processing. In the reduction processing, the processing circuitry 51 generates, from a first partial spectrum relating to a partial area in the spectrum data set at the current number of iterations, a second partial spectrum from which noise has already been reduced. In the error compensation processing, the processing circuitry 51 compensates, with respect to acquired k-space data, an error in a spectrum data set at the current number of iterations. In the optimization processing, the processing circuitry 51 repeats the reduction processing and the error compensation processing as the partial area is changed until predetermined criteria are met, thereby reconstructing a spectrum data set.

FIG. 4 is a diagram schematically showing a spectrum data set. As shown in FIG. 4, a spectrum data set is a data set in which each point of a multidimensional space is allocated a signal intensity value. The multi-dimensional space has a space axis, a time axis, and a chemical shift frequency axis. The space axis is an axis defining a location (voxel) at which a signal intensity value is measured. The time axis is an axis defining a time at which a signal intensity value is acquired. The chemical shift frequency axis is an axis defining a chemical shift frequency component that characterizes a signal intensity value. In FIG. 4, a data space 65 defined by space axes and a time axis is illustrated for easy understanding. The data space 65 may be expressed as a "temporal space". The data space 65 consists of a plurality of sample points 66. Each sample point 66 is assigned a spectrum 67. The spectrum 67 is represented by a signal intensity axis relating to a signal intensity value, which is the measured physical quantity, and the chemical shift frequency axis. The signal intensity value I is proportional to a molecular weight of a molecule corresponding to each chemical shift frequency F0. The chemical shift frequency F0 may be expressed in either Hz or ppm, which are mutually convertible; however, hereinafter, it is expressed in ppm.

As described above, in CSI, data acquisition is continuously performed over a repetition time for each voxel. A single spectrum is generated based on acquired k-space data over the repetition time. The acquisition time of a signal intensity value corresponds to a reference time, such as a start time, a finish time, and an intermediate time, etc. in the repetition time. As described above, in CSI, data acquisition is performed multiple times per voxel. A summation of multiple spectra corresponding to multiple data acquisitions for the number of excitations may be used. In this case, the acquisition time corresponds to a reference time, such as a start time, a finish time, and an intermediate time, etc. of an entire plurality of repetition times. In other words, if a spectrum data set after integration is generated, the time value in the time axis direction has a single value. In this case, the spectrum data set is data of a space defined by a spatial axis and a chemical shift axis, which does not expand with respect to a time axis.

In FIG. 4, the number of dimensions of a spatial dimension of the data space 65 is two dimensions, consisting of a first space X and a second space Y. For example, the first space X corresponds to a phase encoding direction, and the second space Y corresponds to a frequency encoding direction. The signal intensity value I is expressed by I(X, Y, T, F0) based on a first space X, a second space Y, a time T, and a chemical shift frequency F0. The number of dimensions of the space dimension is not limited to two; it may be one dimension or three dimensions.

Through the implementation of the reconstruction function 512, the processing circuitry 51 can reconstruct a molecular image based on the spectrum data set. A molecular image is an image representing a spatial distribution of either a signal intensity or a molecular weight of a designated molecule, or an image in which a signal intensity value or a molecular weight is plotted on each pixel.

Through the implementation of the display control function 513, the processing circuitry 51 displays various types of information on the display 55. For example, the processing circuitry 51 displays a spectrum, a molecular image, and the like on the display 55.

Hereinafter, the reconstruction processing of a spectrum data set performed by the reconstruction apparatus 50 in accordance with a reconstruction program is specifically described. In the following descriptions, suppose that the number of dimensions in the spatial axis of the spectrum data set is two, and the time value is a fixed value Tf. In this case, the signal intensity value of the spectrum data set is expressed by I(X, Y, Tf, F0).

Figure 5:
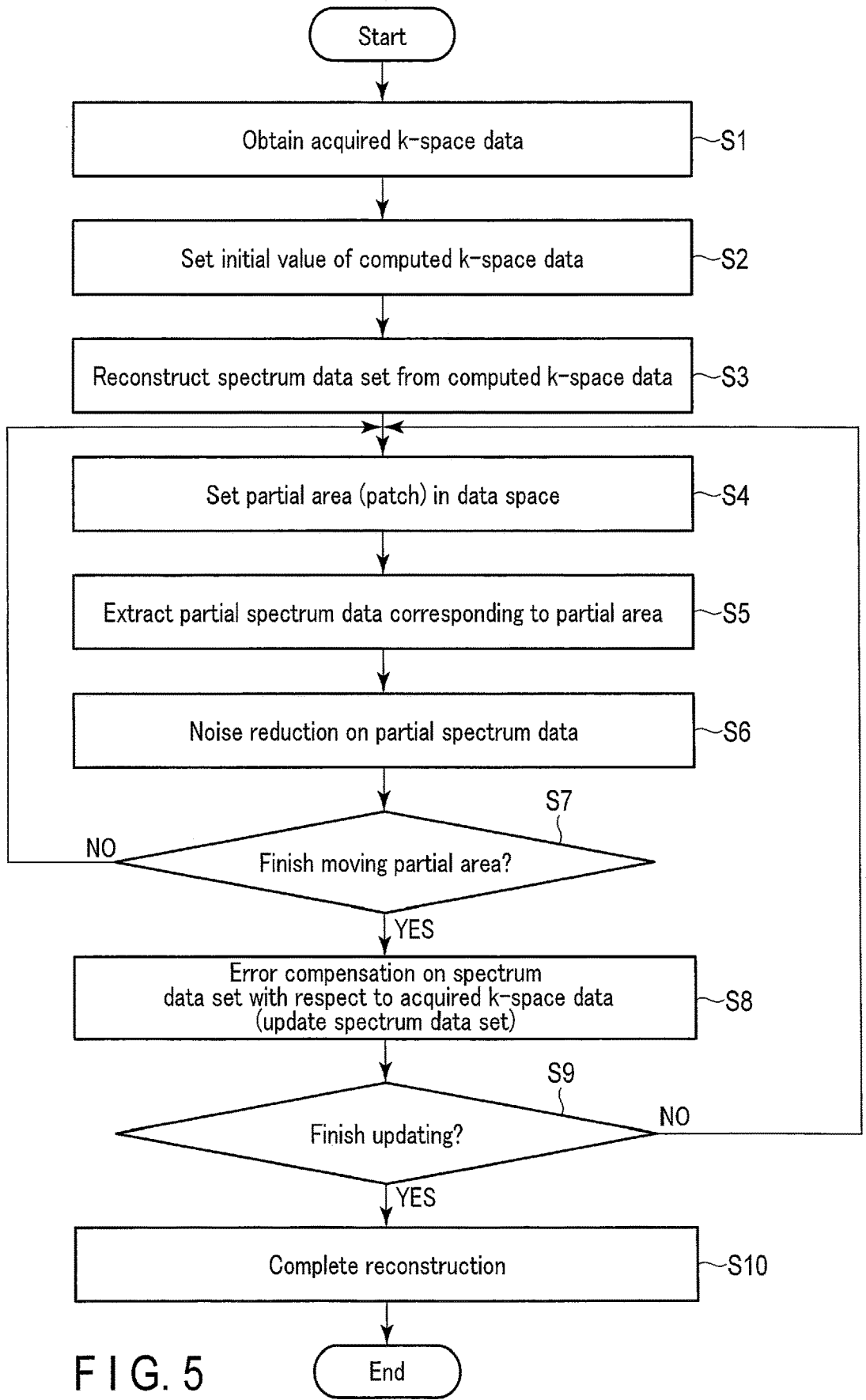
FIG. 5 is a diagram showing a flow of an example of the reconstruction processing of a spectrum data set.
Figure 6:
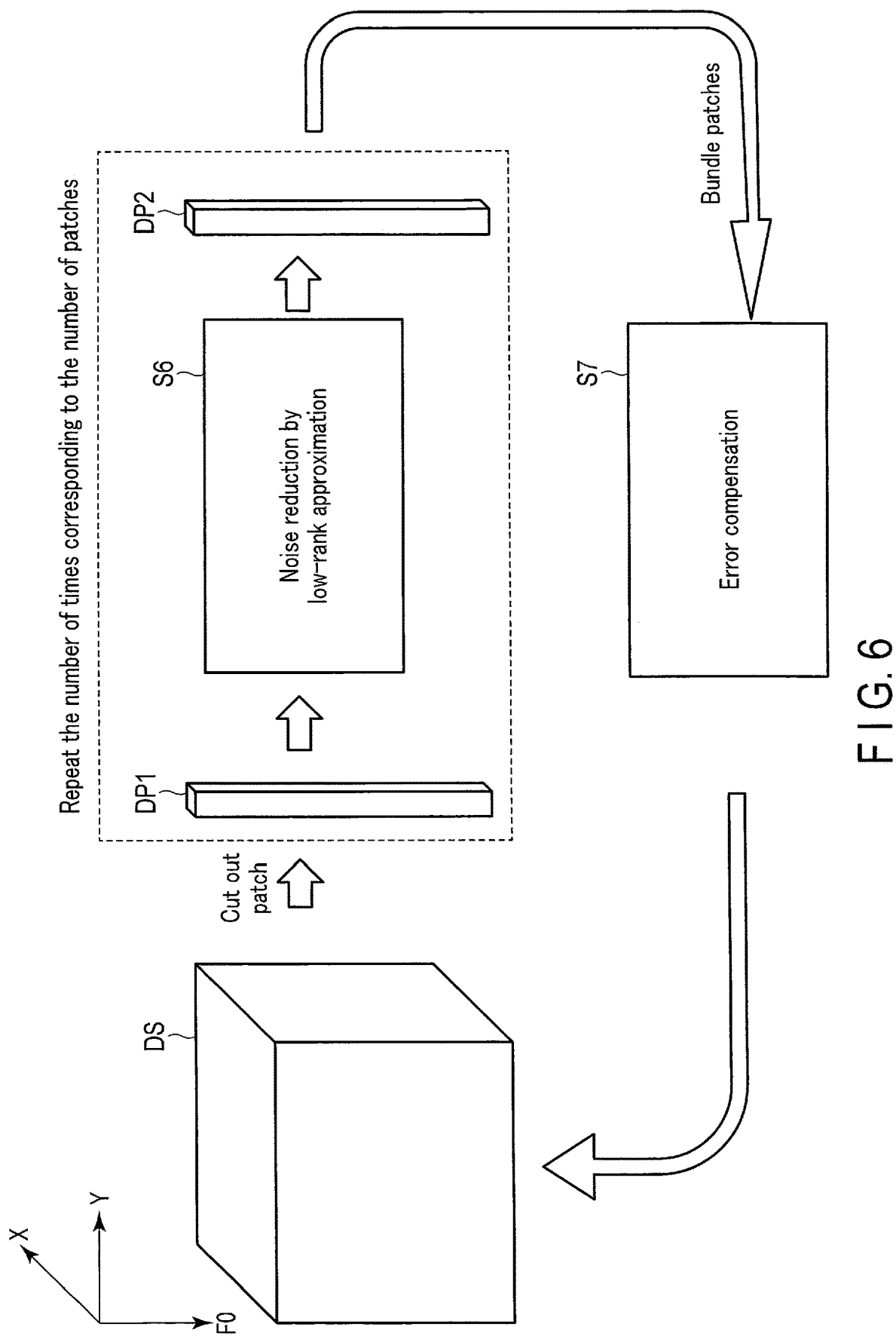
FIG. 6 is a diagram schematically showing an example of processing in steps S4 to S9 in FIG. 5 (noise reduction by low-rank approximation).

FIG. 5 is a diagram showing a flow of an example of the reconstruction processing on a spectrum data set performed by the reconstruction apparatus 50. FIG. 6 schematically shows steps S4 to S9 in FIG. 5.

As shown in FIG. 5, the processing circuitry 51 obtains acquired k-space data through the implementation of the obtainment function 511 (step S1). In step S1, k-space data relating to multiple voxels acquired by CSI is obtained as acquired k-space data. The acquired k-space data may either be fully sampled data with respect to k-space or sparsely sampled data with respect to k-space. Sparse sampling may be sampling carried out in under-sampled data acquisition, such as parallel imaging, etc.

After step S1, the processing circuitry 51 sets an initial value of computed k-space data through the implementation of the reconstruction function 512 (step S2). The computed k-space data is, unlike the acquired k-space data in step S1, k-space data generated by computation and targeted for updating. The initial value may be set at any value. More specifically, the initial value may be set to a uniform value for all the acquisition times or set so as to change over time. For example, the initial value is uniformly set at a zero value for all acquisition times.

In step S2, the processing circuitry 51 may perform error compensation on computed k-space data for which an initial value is set, with respect to acquired k-space data. The details of the error compensation will be described later. Briefly speaking, the processing circuitry 51 calculates errors between computed k-space data for which an initial value is set and acquired k-space data and updates the computed k-space data in accordance with calculated errors.

After step S2, the processing circuitry 51 reconstructs a spectrum data set DS from the computed k-space data for which the initial value is set in step S2 through the implementation of the reconstruction function 512 (step S3). As shown in FIG. 6, the spectrum data set DS is expressed as a three-dimensional space defined by the first space X, the second space Y, and the chemical shift frequency F0. Herein, if the number of voxels in an X direction can be expressed as "#NX" and the number of voxels in a Y direction can be expressed as "#NY", then the spatial size of the data space can be expressed as "#NX*#NY". Each voxel is allocated a spectrum, which is a frequency distribution of a measured intensity value. Supposing the sampling number of a chemical shift frequency is #NF0, a spectrum data set DS has #NX*#NY*#Nf0 data points in total.

After step S3, the processing circuitry 51 sets a partial area in the data space of the spectrum data set DS through the implementation of the reconstruction function 512 (step S4). In the present embodiment, partial area means a local area with respect to a spatial axis. The shape of the partial area may be a polygon, such as a square, a rectangle, a triangle, or a pentagon, a circle, or any other shape. The partial area is not necessarily a spatially continuous single area and it may be two or more areas spatially separated. Hereinafter, suppose the partial area is a single square area to make the following explanation concrete. Such a partial area is called a "patch". If the number of voxels in the X direction of a patch is #NpX and the number of voxels in the Y direction of a patch is #NpY, the spatial size of a patch (hereinafter a "patch size") can be expressed as #NpX*#NpY. The patch size #NpX*#NpY is not limited to a particular size, as long as it is smaller than the data space size #NX*#NY.

After step S4, the processing circuitry 51 extracts spectrum data corresponding to a partial area (patch) set in step S4 (hereinafter, "partial spectrum data") DP1 from the spectrum data set DS, through the implementation of the reconstruction function 512 (step S5). The partial spectrum data DP1 is a set of #NpX*#NpY spectra included in a patch. The partial spectrum data DP1 may be called "patch data".

After step S5, the processing circuitry 51 performs noise reduction processing on the partial spectrum data DP1 in step S5, through the implementation of the reconstruction function 512 (step S6). In step S6, the processing circuitry 51 generates noise-reduced partial data by performing low-rank approximation on the partial spectrum data DP1. The noise targeted for reduction includes not only noise caused by a non-uniform static magnetic field but also noise caused by data acquisition, noise caused by signal processing performed on MR signals, and noise caused by data processing performed on k-space data and spectra; thus, the targeted noise is not limited to a particular type of noise.

The noise reduction by low-rank approximation is, roughly speaking, performed in the following sequence. The processing circuitry 51 conducts matrix decomposition on partial spectrum data to calculate a plurality of bases, and selects therefrom one or more bases that meet criteria relating to a contribution rate, and applies the one or more selected bases to the partial spectrum data to generate noise-reduced partial spectrum data. As matrix decomposition, principal component analysis (PCA), singular value decomposition, and non-negative value matrix factor decomposition, etc. may be performed. Hereinafter, principal component analysis will be used as an example to specifically explain the noise reduction.

Herein, the patch size is 5*5, and the number of sample points of a chemical shift frequency is 1024. In this case, the signal intensity value I, namely a spectrum, is regarded as a vector having 1024 values. By performing principal component analysis on 25 spectra, 25 orthogonal base vectors are calculated. A contribution rate is computed for each orthogonal base vector. One or more base vectors are selected based on criteria relating to a contribution rate. As criteria, a condition that a contribution rate is greater than a predetermined value and a condition that a base vector has a top-N(N is an integer) contribution rate may be set. For example, three base vectors, which are the top three in the contribution rate, are selected. Hereinafter, the selected base vectors will be called "PCA bases". Next, for each of 25 spectra, three coefficients (hereinafter "PCA coefficients") are calculated by performing an arithmetic operation to determine an inner product of the spectrum and three PCA bases, and a linear sum of each inner product of three PCA bases and three PCA coefficients is calculated. The calculated linear sum corresponds to a noise-reduced spectrum.

In the above-described example, the spatial size (patch size) of the noise-reduced partial spectrum data DP1 and the spatial size (partial size) of the partial spectrum data DP2 before noise reduction are both 5*5. However, the present embodiment is not limited to this example, and the patch size after the noise reduction may be smaller than that before the noise reduction. For example, the patch size after the noise reduction may be set to 3*3 or 1*1, compared to the patch size 5*5 before the noise reduction processing. The reduction of patch size may be realized by synthesizing spectra of voxels either after or before noise reduction. This enables averaging the spectra spatially.

After step S6, through the implementation of the reconstruction function 512, it is determined whether or not the moving of a partial area (patch) should be finished (step S7). In step S7, the processing circuitry 51 determines whether or not a condition for terminating moving is met. As the condition for terminating moving, a condition that a partial area is set for all voxels that constitutes either an entire area or a region of interest of a spectrum data set, etc. may be set. If it is determined that the moving should not be finished (No in step S7), the processing circuitry 51 sets a partial area to a different position of a spectrum data set at the current number of iterations (step S4). A mode of movement is not limited particularly. The partial area may be set adjacent to, separate from, or partially overlapping a partial area at the previous number of iterations. The shape and size may be the same between the partial area at the previous number of iterations and the partial area at the current number of iterations, or both or either of the shape and size may differ therebetween. The processing circuitry 51 repeats steps S4 to S7 for each partial area until it is determined that the condition for terminating moving is met in step S7. The "number of iterations" is the number of times of performing steps S4 through S9, in other words, the number of times of performing the noise reduction (step S6) and the error compensation (step S8). The "current number of iterations" means the number of iterations at the time of processing.

When it is determined that the moving of the partial area should be terminated in step S7 (Yes in step S7), the processing circuitry 51 compensates errors in the spectrum data set DS at the current number of iterations with respect to the acquired k-space data, through the implementation of the reconstruction function 512 (step S8). Specifically, in step S8, the processing circuitry 51 computes computed k-space data from the synthesized spectrum data set obtained by synthesizing the partial spectrum data DP2 after being subjected to noise reduction and the spectrum data set DS at the current number of iterations based on errors between the computed k-space data and the acquired k-space data.

There are roughly two types of error compensation in step S8. The first type is a method of compensating errors of a spectrum data set DS with respect to a single set of acquired k-space data. The second type is a method of compensating errors of a spectrum data set DS with respect to two sets of acquired k-space data. Any error compensation method may be adopted as the first type of the error compensation and the second type of the error compensation; however, suppose a conjugate gradient method is adopted in the present embodiment.

Figure 7:
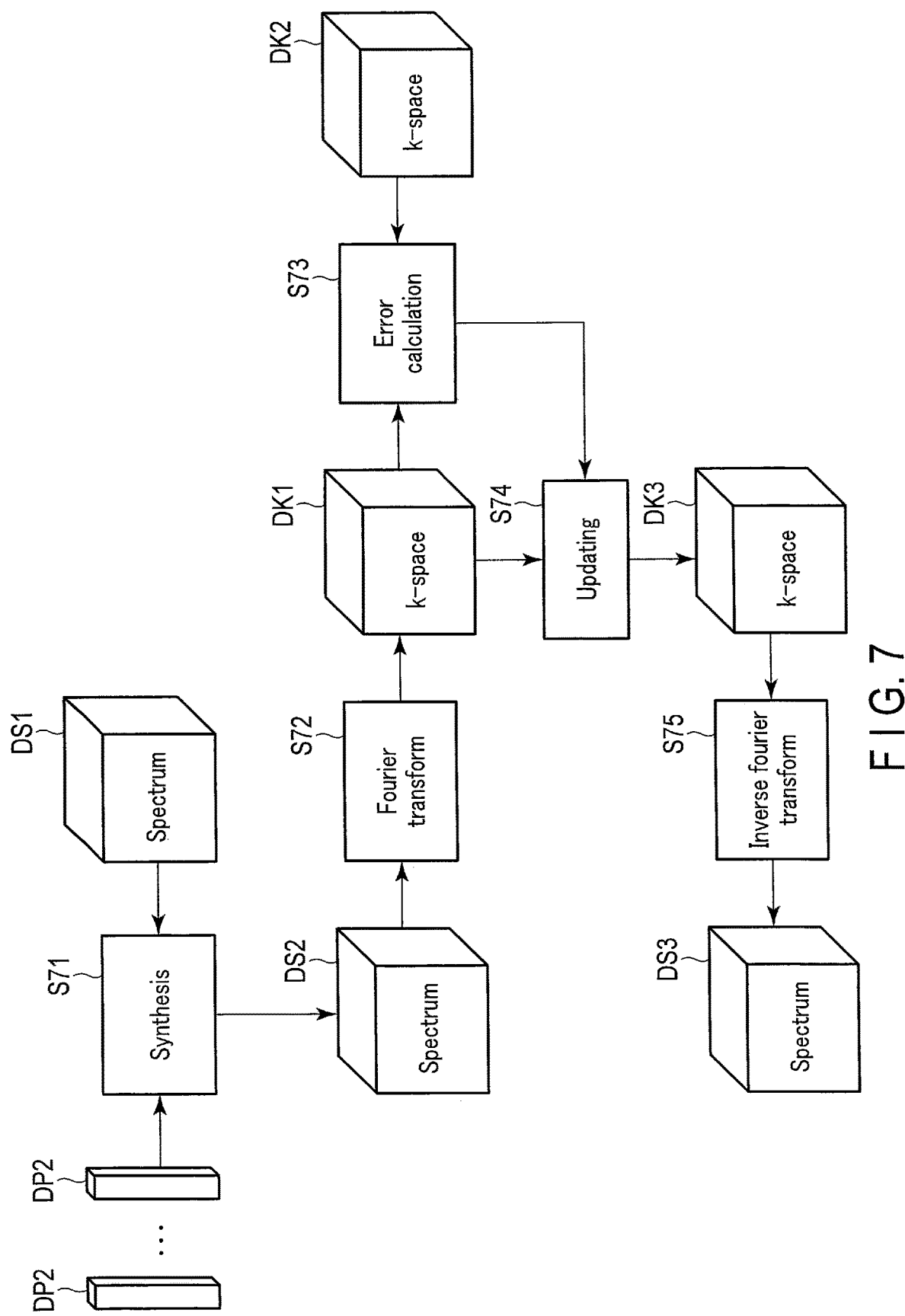
FIG. 7 is a diagram schematically showing a flow of an example of a first type of error compensation processing.

FIG. 7 is a diagram schematically showing a flow of an example of the first type of error compensation processing. As shown in FIG. 7, the processing circuitry 51 synthesizes the partial spectrum data DP2 after being subjected to noise reduction and the spectrum data set DS1 at the current number of iterations to generate a synthesized spectrum data set DS2 (step S71). At the time of starting step S71, multiple sets of the partial spectrum data DP2 that have been subjected to the noise reduction have been generated in correspondence to the number of iterations of step S4 through step S7. The multiple sets of the partial spectrum data DP2 corresponding to the number of times of repeating step S4 through S7 are synthesized with the spectrum data set DS1. Various methods can be adopted for the synthesis in step S71. For example, in step S71, the partial spectrum data DP2 corresponding to a particular patch may be replaced with data corresponding to the patch included in the spectrum data set DS1, or average data of the partial spectrum data DP2 and the data corresponding to said patch included in the spectrum data set DS1 may be replaced with the data corresponding to said patch.

After step S71, the processing circuitry 51 performs Fourier transform on the synthesized spectrum data set DS2 and generates computed k-space data DK1 (step S72). The Fourier transform method is not limited to a particular method, and a grid method, etc. using fast Fourier transform may be performed. In the present embodiment, the Fourier transform is a transform from a real space to a frequency space, and the inverse Fourier transform is a transform from a frequency space to a real space. After step S72, the processing circuitry 51 calculates errors between the computed k-space data DK1 generated in step S72 and the acquired k-space data DK2 obtained in step S1 (step S73). Errors may be any indicators representing differences between the computed k-space data DK1 and the acquired k-space data DK2; for example, a ratio or a difference, etc. of data values of each sample point in the computed k-space data DK1 and the acquired k-space data DK2.

After step S73, the processing circuitry 51 updates the computed k-space data DK1 in accordance with the errors calculated in step S73 and generates updated k-space data DK3 (step S74). For example, the processing circuitry 51 updates the data by adding up the errors at each sample point to the computed k-space data DK1. After step S74, the processing circuitry 51 performs the inverse Fourier transform on the k-space data DK3 and generates an updated spectrum data set DS3 (step S75). The inverse Fourier transform method is not limited to a particular method, and the inverse fast Fourier transform or a gridding method, etc. may be adopted.

By the above-described processing, the error compensation of the partial spectrum data DP2 for each partial area (patch) with respect to the acquired k-space data DK2, in other words, updating the spectrum data set DS1, is achieved. In other words, fitting of the noise-reduced partial spectrum data DP2 with respect to the acquired k-space data DK2 is performed for each partial area (patch).

FIG. 8 is a diagram schematically showing a flow of an example of a second type of error compensation processing. As shown in FIG. 8, the processing circuitry 51 updates the spectrum data set DS1 at the current number of iterations based on the first errors between the computed k-space data DK1 and the first acquired k-space data DK21, and the second errors between the computed k-space data DK1 and the second acquired k-space data DK22. The first acquired k-space data DK21 is k-space data acquired by a first pulse sequence. The second acquired k-space data DK22 is k-space data acquired by a second pulse sequence. Although the first pulse sequence and the second pulse sequence belong to the same protocol, assume that the first pulse sequence is performed in advance of the second pulse sequence. For example, a PRESS method is adopted as a first pulse sequence, and a PRESS-EPSI method is adopted as a second pulse sequence. In this case, the PRESS method has a higher image quality reliability but a lower spatial resolution compared to the PRESS-EPSI method. Thus, the second type of the error compensation is to compensate errors in the first acquired k-space data DK21 and the second acquired k-space data DK22 acquired by two pulse sequences of different characteristics.

As shown in FIG. 8, the processing circuitry 51 first synthesizes the partial spectrum data DP2 after being subjected to noise reduction and the spectrum data set DS1 at the current number of iterations to generate a synthesized spectrum data set DS2 (step S71). After step S71, the processing circuitry 51 performs the Fourier transform on the synthesized spectrum data set DS2 and generates computed k-space data (step S72).

After step S72, the processing circuitry 51 calculates first errors between the computed k-space data DK1 generated in step S72 and the first acquired k-space data DK21 (step S731). The processing circuitry 51 calculates second errors between the same computed k-space data DK1 and the second acquired k-space data DK22 (step S732).

After steps S731 and S732, the processing circuitry 51 updates the computed k-space data DK1 in accordance with the first errors obtained in step S731 and the second errors obtained in step S732, and generates updated k-space data DK3 (step S74). For example, the processing circuitry 51 updates the data by adding up an average or a weighted average, etc. of the first errors and the second errors at each sample point to the computed k-space data DK1. After step S74, the processing circuitry 51 performs the inverse Fourier transform on the k-space data DK3 and generates an updated spectrum data set DS3 (step S75).

By the above-described processing, the error compensation of the partial spectrum data DP2 with respect to the acquired k-space data DK2, in other words, updating the spectrum data set DS1, is achieved.

In the second type of the error compensation, errors are compensated in two sets of acquired k-space data acquired by two types of pulse sequences; thus, the accuracy in the error compensation is improved compared to the first type in which errors are compensated for a single set of acquired k-space data. Since the error compensation is performed on two sets of acquired k-space data acquired by the pulse sequences in which the accuracy is reversed between the spatial resolution and the image quality reliability, which are in a trade-off relationship, it is possible to achieve the spatial resolution and the image quality reliability at high accuracy. In contrast, error compensation is performed on a single set of acquired k-space data in the first type of error compensation, and therefore it is possible to save a calculation cost compared to the second type of error compensation.

After step S8, through the implementation of the reconstruction function 512, the processing circuitry 51 determines whether or not the updating should be finished (step S9). In step S9, the processing circuitry 51 determines whether or not the predetermined condition for terminating updating is met. It suffices that the conditions for terminating updating are, for example, a condition that a predetermined number of updates is exceeded and a condition that an amount of updating a spectrum data set is less than a predetermined value. If the conditions for terminating updating are not met, the processing circuitry 51 determines that the updating is not terminated and sets the partial area to an initial position and performs steps S4 to S9. The processing circuitry 51 repeats step S4 through step S9 until the condition for terminating updating is met. This repetition of step S4 through step S9 corresponds to the optimization process in which the noise reduction (step S6) and the error compensation (step S9) are repeated with the partial area moved, until the condition for terminating updating is met.

The spectrum reconstruction including the repetition of steps S6 to S9 returns to the processing of minimizing an object function, which is shown below as (1). The processing circuitry 51 performs minimization of the object function shown in Expression (1) with an ADMM (alternating direction method of multipliers) and a penalty method, etc. The first term is a mathematical expression of the error compensation by the conjugate gradient method in step S7. F represents the Fourier transform, S represents a coil sensitivity, x represents a spectrum, and y represents k-space data. The second term is a mathematical expression of the noise reduction in step S6. $D(x)$ is a mathematical expression of the noise reduction with respect to the spectrum x in each partial area. $\lambda$ is a weighting coefficient. $\|\cdot\|_2$ represents an L2 norm. P represents all patches.

$$\operatorname{argmin}_{x} \|FSx - y\|_2^2 + \lambda \sum_{x_{patch} \in P} \|x_{patch} - D(x_{patch})\|_2^2 \quad (1)$$

As described above, x and y in Expression (1) have, in the present embodiment, a chemical shift frequency axis F0 in addition to the dimensions of the first spatial axis X and the second spatial axis Y. For example, in the case of full sampling, the number of dimensions of x and y is #NX*#NY**NF0. As the coil sensitivity S, it suffices that a sensitivity to water estimated by a pulse sequence such as an SPGR or an ESPRIT is used. In the case of one coil, it suffices that the coil sensitivity S is set at a unit matrix.

The data acquisition in the present embodiment is full sampling; however, the data acquisition is applicable to sparse acquisition such as parallel imaging, etc. The object function in Expression (1) may be combined with other terms such as a compressed sensing term, etc.

If it is determined that the updating should be terminated in step S9 (Yes in step S9), the processing circuitry 51 completes the reconstruction through the implementation of the reconstruction function 512 (step S10). In step S10, the processing circuitry 51 outputs the spectrum data set at the stage of performing step S10 as a reconstruction completed version. The spectrum data set of the reconstruction-completed version is stored in the memory 53. The processing circuitry 51 may extract a spectrum in a voxel of interest from the spectrum data set of the reconstruction completed version and display the spectrum on the display 55, or may reconstruct a molecular image showing a spatial distribution of a signal intensity value or a molecular weight of a molecule of interest based on a spectrum data set of the reconstruction completed version and display the molecular image on the display 55.

After step S10, the reconstruction processing of the spectrum data set shown in FIG. 5 is finished.

The flow of the reconstruction process shown in FIG. 5 is an example and can be modified in various ways, without being limited to this example. For example, the order of performing the determination of the condition for terminating updating the spectrum reconstruction (step S9) and the determination of the condition for terminating moving the partial area (step S7) may be reversed. In this case, a step of determining a final condition for terminating may be provided after the finishing of the determination of the condition for terminating updating the spectrum reconstruction (step S9) and the determination of the condition for terminating moving the partial area (step S7). In this determination step, the processing circuitry 51 determines whether or not steps S4 to S9 should be repeated. As conditions for determining that the process should be finally terminated, for example, a condition that steps S4 through S9 are repeated the predetermined number of times, a condition that an amount of updating in the spectrum data set at the final number of iterations is smaller than a predetermined value, and the like, may be set. The processing circuitry 51 repeats steps S4 to S9 until the final condition for terminating the process is met. Thus, improvement in the accuracy of the spectrum reconstruction can be expected. In the foregoing embodiment, the noise reduction and the error compensation are performed for each partial area; however, the noise reduction and the error compensation may be performed for each of multiple partial areas.

In the present embodiment, since the noise reduction and the error compensation are repeated in a unit of partial area (a patch) as described above, it is possible to reduce a non-uniformity of a magnetic field included in a spectrum data set. The technique disclosed in the non-patent document assumes the SPICE method using a PS model in which a space and a spectrum are separated, in other words, assumes that a space and a spectrum are separable; however, if this assumption does not hold, the accuracy of the reconstruction would be degraded. According to the embodiment, on the other hand, a space and a spectrum are not separated; therefore, it is possible to improve the accuracy of the reconstruction even when the assumption that a space and a spectrum are separable does not hold true. It is also possible to perform reconstruction as the non-uniformity in the magnetic field is corrected.

In the foregoing example, the noise reduction in step S6 is performed through low-rank approximation. However, the present embodiment is not limited thereto. The processing circuitry 51 may perform noise reduction with a machine learning model. Hereinafter, the reconstruction processing performed on a spectrum data set using noise reduction by a machine learning model is described.

FIG. 9 schematically shows processes of steps S4 to S9 in FIG. 5. In the present embodiment, step S6 in FIGS. 5 and 6 is replaced with step S62. In step S62, the processing circuitry 51 performs noise reduction using a machine learning model on the partial spectrum data (patch data) DP1 of the partial area (patch) extracted in step S5, and generates noise-reduced partial spectrum data DP2.

FIG. 10 is a diagram showing an example of an input and an output of a machine learning model. As shown in FIG. 10, the machine learning model is a neural network to which spectra are input and which is trained to output noise-reduced spectra. Assume that the machine learning model outputs a single noise-reduced spectrum upon input of a single spectrum of one voxel. The processing circuitry 51 applies multiple spectra included in a partial area individually to the machine learning model and generates a plurality of noise-reduced spectra. It is assumed that a spectrum in the present embodiment is a waveform of a signal intensity value relating to a frequency axis direction (hereinafter "spectrum waveform").

The training of the machine learning model may be conducted by the reconstruction apparatus 50 or by a computer for machine training. Hereinafter, assume that the training of the machine learning model is performed by the processing circuitry 51 of the reconstruction apparatus 50.

In the training stage, the processing circuitry 51 obtains multiple training samples collected by MR spectroscopy for various types of subjects and voxels. The training samples include training samples for input and training samples for teaching. The training samples for input are spectra acquired by a discretionarily chosen method, and the training samples for teaching are spectra from which noise included in the training samples for input is reduced. As the training samples for teaching, a spectrum is generated by performing low-rank approximation on a training sample for input. The processing circuitry 51 trains the learning parameters based on the supervised learning using multiple training samples with a discretionarily chosen optimization method, such as a stochastic gradient descent method, in such a manner that errors between the output from the machine learning model based on the input training sample and the training samples for teaching are minimized. The learning parameters are those that are set in a machine learning model, for example a weighting coefficient and a bias, etc.

Conducting machine learning in such a manner allows generation of a machine learning model that imitates low-rank approximation. The processing circuitry 51 can reduce the noise in partial spectrum data of a partial area at a low calculation cost and within a short time, by using a machine learning model.

In the foregoing example, the training samples for teaching are spectra to which a low-rank approximation is performed; however, the present embodiment is not limited to this example. For example, as the training samples for teaching, a real spectrum in which a signal-to-noise ratio is increased by locally repeating imaging, a spectrum to which any type of signal processing is performed to reduce noise, such as smoothing and averaging, or the like may be used in addition to the low-rank approximation.

The spectra in the forgoing example is a spectrum waveform acquired by CSI. However, the present embodiment is not limited thereto. The spectra in the present example are not limited to a spectrum waveform and may have multiple aspects including a parameter that characterizes a spectrum waveform (hereinafter "spectrum parameter"). The spectrum parameters include a chemical shift frequency, a signal intensity value of a peak of a spectrum waveform, a molecular weight (an M0 value), a half width, etc. The training samples may be artificially generated spectra. Hereinafter, the training of the machine learning model in this case is described.

Figure 11:
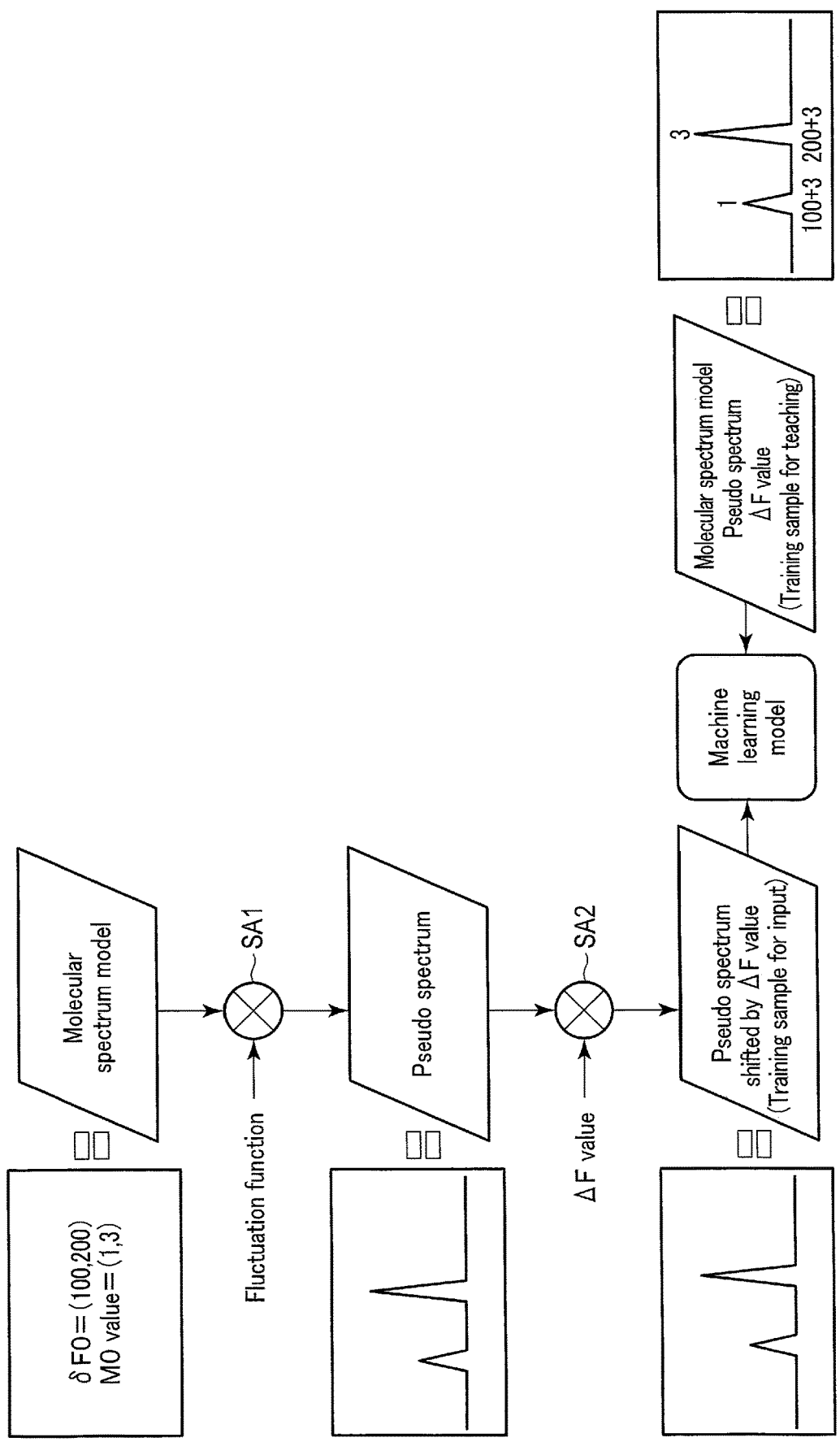
FIG. 11 is a diagram schematically showing a process of generating training samples used to train a machine learning model.

FIG. 11 is a diagram schematically showing a process of generating a training sample used to train a machine learning model. As shown in FIG. 11, the processing circuitry 51 obtains molecule spectrum models of respective molecules as training samples. The molecules are those constituting metabolites included in an area targeted for CSI and there is variety in accordance with the targeted area. The molecule spectrum model is numerical value data of a spectrum parameter relating to the molecule. In the present example, the spectrum parameter of the molecule spectrum model is a combination of a chemical shift frequency value (a δF0 value) and a signal intensity value (an M0 value). A δF0 value is a standard chemical shift frequency value of each peak in a corresponding molecule spectrum model. An M0 value is a signal intensity value of a peak corresponding to each δF0 value. The signal intensity value has a value proportional to a molecular weight of the targeted molecule, and more strictly, an amount of protons of hydrogen atoms contained in the targeted molecule. An M0 value is expressed with a ratio to a standard signal intensity value, namely in an arbitrary unit [AU]. The δF0 value and an M0 value may be measured based on a nuclear magnetic resonance (NMR) measuring device, etc. or may be computed from a prediction calculation based on physical principles of an NMR phenomenon. These values may be obtained from a database storing δF0 values and M0 values of multiple molecules acquired by the above-described methods. If numerical ranges, not numerical values, are stored in the database, discretionarily selected numerical values in the numerical ranges may be used. In the case of FIG. 11, the δF0 values are 100 ppm and 200 ppm. In the case of FIG. 11, the M0 values are 1 AU and 3 AU.

After the training samples are obtained, the processing circuitry 51 generates a pseudo spectrum by applying a fluctuating function to a molecule spectrum model (step SA1). A Gaussian function is a typical fluctuation function; however, any function may be used as a fluctuation function. A pseudo spectrum is an artificial spectrum waveform calculated based on a molecule model. A frequency corresponding to a peak of a pseudo spectrum corresponds to a δF0 value, and a crest factor corresponds to an M0 value.

After step SA1, the processing circuitry 51 shifts the pseudo spectrum by a ΔF value in a frequency axis direction based on the ΔF value (step SA2). A ΔF value corresponds to an amount of deviation of a chemical shift frequency due to the non-uniformity of magnetic field. The ΔF value may be generated randomly or pseudo-randomly by a discretionarily selected randomizer. Preferably, the ΔF value is limited to a range of a realistic frequency deviation amount. The ΔF value may be set to a value such as . . . −3, −2, −1, +1, +2, +3, . . . , for example. The ΔF value is not of course limited to an integer, as long as it is a real number.

The pseudo spectrum shifted by a ΔF value is used as a training sample for input. The combination of the molecule spectrum model, the pseudo spectrum model, and the ΔF value are, on the other hand, used as training samples for teaching. The number of training samples for input and training samples for teaching can be increased per molecule by changing a parameter of a fluctuation function or a random number seed of a ΔF value, etc. The processing circuitry 51 trains the learning parameters of the machine learning model based on the supervised learning using the training samples for input and training samples for teaching. With such machine learning, a machine learning model to which a spectrum is input and which outputs a molecule spectrum model corresponding to the spectrum, a spectrum with a corrected deviation of a magnetic field, and a deviation amount of a magnetic field can be generated. The processing circuitry 51 is capable of displaying a molecule spectrum model, a spectrum in which a magnetic field deviation is corrected, and an amount of magnetic field deviation on the display 55 for presentation to a user. The processing circuitry 51 is capable of generating a pseudo spectrum for each voxel and generating a molecular image of a targeted molecule based on multiple pseudo spectra.

The training samples for teaching are not limited to combinations of a molecular spectrum model, a pseudo spectrum model and a ΔF value; they maybe combinations of a molecular spectrum and a ΔF value or just a pseudo spectrum. In this case, the processing circuitry 51 is capable of generating a pseudo spectrum by applying a fluctuation function to a molecular spectrum model that is output from the machine learning model.

The relationship between the number of input spectra and output spectra in the machine learning model is not limited to a one-to-one relationship; it may be multiple numbers to one, one to multiple numbers, or multiple numbers to multiple numbers. Even for these cases, it is possible to train the learning parameters of the machine learning model based on the supervised learning using the corresponding number of training samples for input and the corresponding number of training samples for teaching.

The training of the machine learning model using artificially generated spectra is thus finished.

As described above, the processing circuitry 51 is able to reduce noise in a spectrum using a machine learning model. The use of a machine learning model negates a need to perform low-rank approximation for each partial area, which requires a high calculation cost; therefore, it is possible to reduce a calculation cost and to shorten a processing time. It is also possible to reduce a particular type of noise, etc. that cannot be reduced by a low-rank approximation, in accordance with a combination of the training samples for input and the training samples for teaching at the time of machine learning.

As described above, the processing circuitry 51 is able to reduce noise in a spectrum using a low rank approximation or a machine learning model. Which method should be used to reduce noise may be chosen discretionarily by a user through the input interface 57, etc., or may be predetermined.

Hereinafter, an example of another type of reconstruction processing performed on a spectrum data set using low-rank approximation is described.

FIG. 12 is a diagram showing a flow of an example of other reconstruction of a spectrum data set by the reconstruction apparatus 50, using low-rank approximation. As shown in FIG. 12, the processing circuitry 51 acquires acquired k-space data through the implementation of the obtainment function 511 (step S1201). The processing in step S1201 is similar to that in step S1.

After step S1201, the processing circuitry 51 sets a reference spectrum through the implementation of the reconstruction function 512 (step S1202). A reference spectrum is a spectrum set. A spectrum set is, for example, a set of pre-measured spectra collected for all candidate molecules, each obtained by MRS for a single molecule, a set of logical spectra collected for all candidates, each obtained by calculation of information of a single molecule, or a set of pre-measured spectra collected for all candidate molecules, each obtained by MRS for each molecule mixed at a given mixture ratio.

After step S1202, the processing circuitry 51 tentatively reconstructs tentative spectrum data corresponding to an entire targeted area (tentative spectrum data set) obtained in step S1201 through the implementation of the reconstruction function 512 (step S1203). Specifically, the processing circuitry 51 inputs acquired k-space data and outputs a tentative spectrum data set by performing tentative reconstruction on the input acquired k-space data in both a spatial direction and a temporal direction. The data format of the tentative spectrum data set is the same as that of the spectrum data set DS shown in FIG. 6. Tentative reconstruction is selected as appropriate from arbitrarily selected reconstruction means. As an example, the tentative reconstruction may be the fast Fourier transform. As another example, the tentative reconstruction may be achieved by a parallel imaging method in a spatial direction and fitting in a temporal direction based on a T2 attenuation model of a signal. As another example, the tentative reconstruction may be achieved by a compressed sensing method in a spatial direction and fitting in a temporal direction based on a low-rank spectrum.

After step S1203, the processing circuitry 51 sets a partial area in the data space of the spectrum data set through the implementation of the reconstruction function 512 (step S1204). Step S1204 is similar to step S4.

After step S1204, the processing circuitry 51 outputs a corrected static magnetic field deviation and noise-reduced tentative spectrum data through the implementation of the reconstruction function 512 (step S1205). Specifically, the processing circuitry 51 first extracts a tentative spectrum data set corresponding to the partial area (patch) set in step S1204 from a tentative spectrum data set. The tentative spectrum data is a set of #NpX*#NpY tentative spectra included in a patch. Next, the processing circuitry 51 outputs a corrected static magnetic field deviation and noise-reduced tentative spectrum data based on tentative spectrum data, a reference spectrum, and an estimated static magnetic field deviation. A static magnetic field deviation is, for example, the above-described ΔF value or a scaled ΔF value. By inputting tentative spectrum data, a reference spectrum, and a static magnetic field deviation, it can be expected that tentative spectrum data and a static magnetic field deviation having more accurate values than the input values can be output.

After step S1205, through the implementation of the reconstruction function 512, the processing circuitry 51 determines whether or not the moving of a partial area (patch) should be finished (step S1206). Step S1206 is similar to step S7.

When it is determined that the moving of the partial area should be terminated in step S1206 (Yes in step S1206), the processing circuitry 51 compensates errors in the tentative spectrum data set at the current number of iterations with respect to the acquired k-space data, through the implementation of the reconstruction function 512 (step S1207). Specifically, in step S1207, the processing circuitry 51 outputs an error-compensated tentative spectrum data set based on noise-reduced tentative spectrum data and acquired k-space data.

The error compensation is performed with the following procedures, for example. First, the processing circuitry 51 bundles noise-reduced tentative spectra as a tentative spectrum data set. The tentative spectrum data set, which is a bundle of noise-reduced tentative spectra, is data of an x-y-f space. A noise-reduced tentative spectrum has a data size of 3×3×1024, and a bundle of noise-reduced tentative spectra, namely the tentative spectrum data set, has a data size of 16×16×1024. Next, the processing circuitry 51 performs the Fourier transform on the tentative spectrum data set and converts it to kx-ky-f space data. Then, the processing circuitry 51 inputs acquired k-space data. Assume that the acquired k-space data is kx-ky-t space data. The processing circuitry 51 performs the Fourier transform with respect to the time t axis on the acquired k-space data to convert it to kx-ky-f space data. Subsequently, the processing circuitry 51 optimizes the tentative spectrum data set of the kx-ky-f space by a conjugate gradient method so as to minimize squared errors of differences between the tentative spectrum data set of the kx-ky-f space and the acquired k-space data of the kx-ky-f space. The optimized tentative spectrum data set is output as an error-compensated tentative spectrum data set.

After step S1207, through the implementation of the reconstruction function 512, the processing circuitry 51 determines whether or not the updating should be finished (step S1208). In step S1208, the processing circuitry 51 determines whether or not the predetermined condition for terminating updating is met. It suffices that the conditions for terminating updating are, for example, a condition that a predetermined number of updates is exceeded and a condition that an amount of updating a spectrum data set is less than a predetermined value. If the conditions for terminating updating are not met, the processing circuitry 51 determines that the updating is not terminated and sets the partial area to an initial location and performs steps S1204 to S1208. The processing circuitry 51 repeats step S1204 through step S1208 until the condition for terminating updating is met. This repetition of step S1204 through step S1208 corresponds to the optimization process in which the noise reduction (step S1205) and the error compensation (step S1207) are repeated with the partial area being moved, until the condition for terminating updating is met.

The spectrum reconstruction including the repetition of steps S1206 to S1208 returns to the processing of minimizing an objective function, which is shown below as Expression (1). In the reconstruction processing shown in FIG. 12, F in Expression (1) represents the Fourier transform in both of a spatial direction and a temporal direction. S in Expression (1) represents a coil sensitivity to all spatial pixels and all frequencies, for example the same coil sensitivity to all frequencies. The coil sensitivity to all frequencies may not be strictly the same and the coil sensitivities may be different between frequencies. x in Expression (1) represents a spectrum for all spatial pixels and frequencies reconstructed with respect to both the spatial direction and the temporal direction. y in Expression (1) represents k-space data with respect to all k-space locations and all times that are not reconstructed with respect to both the spatial direction and the temporal direction.

If it is determined that the updating should be terminated in step S1208 (Yes in step S1208), the processing circuitry 51 completes the reconstruction through the implementation of the reconstruction function 512 (step S1209). In step S1209, the processing circuitry 51 outputs the spectrum data set at the stage of performing step S1209 as a reconstruction completed version. The spectrum data set of the reconstruction-completed version is stored in the memory 53. The processing circuitry 51 may extract a spectrum in a voxel of interest from the spectrum data set of the reconstruction completed version and display the spectrum on the display 55, or may reconstruct a molecular image showing a spatial distribution of a signal intensity value or a molecular weight of a molecule of interest based on a spectrum data set of the reconstruction completed version and display the molecular image on the display 55.

After step S1209, the reconstruction processing of the spectrum data set shown in FIG. 12 is finished.

Next, an example of another reconstruction of a spectrum data set using a machine learning model is described.

Figure 13:
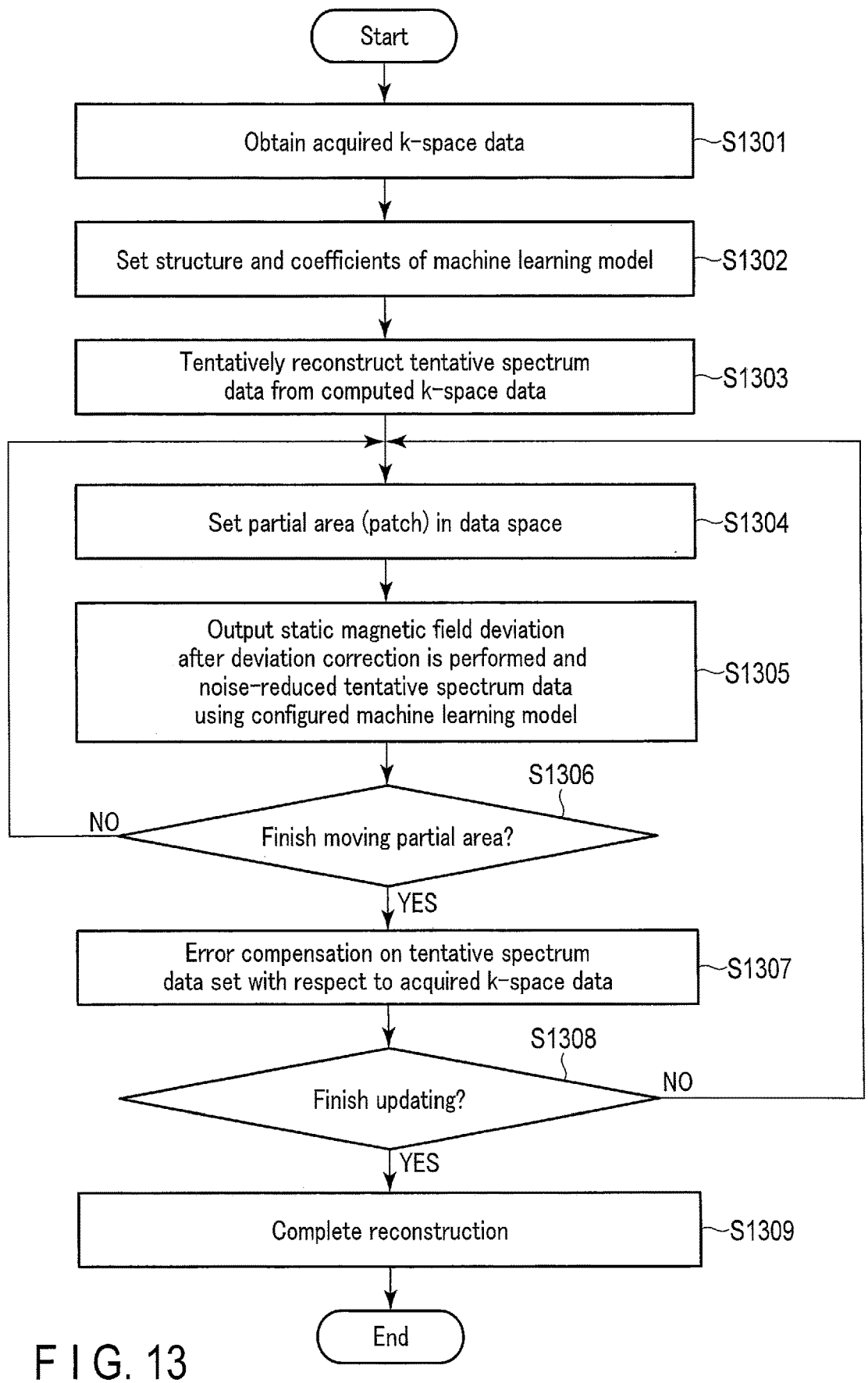
FIG. 13 is a diagram showing a flow of another example of another reconstruction of a spectrum data set.

FIG. 13 is a diagram showing a flow of an example of another reconstruction of a spectrum data set by the reconstruction apparatus 50, using a machine learning model.

As shown in FIG. 13, the processing circuitry 51 acquires acquired k-space data through the implementation of the obtainment function 511 (step S1301). The processing in step S1301 is similar to that in step S1.

After step S1301, the processing circuitry 51 sets a structure and coefficients of the machine learning model through the implementation of the reconstruction function 512 (step S1302). The machine learning model according to step S1302 is a neural network to which a spectrum is input and is trained to output a noise-reduced spectrum, as shown in FIG. 10. In the memory 53, the structure and coefficients of the trained machine learning model are stored. The processing circuitry 51 reads the structure and coefficients from the memory 53 and sets them in a standard machine learning model. Hereinafter, a machine learning model in which the structure and coefficients are set will be referred to as a "configured machine learning model".

After step S1302, the processing circuitry 51 tentatively reconstructs a spectrum data set from the acquired k-space data obtained in step S1301 through the implementation of the reconstruction function 512 (step S1303). Step S1303 is similar to step S1203.

After step S1303, the processing circuitry 51 sets a partial area in the data space of the tentative spectrum data set through the implementation of the reconstruction function 512 (step S1304). Step S1304 is similar to step S4.

After step S1304, the processing circuitry 51 outputs a static magnetic field deviation after deviation correction is performed and noise-reduced tentative spectrum data through the implementation of the reconstruction function 512 (step S1305). Specifically, the processing circuitry 51 first extracts a tentative spectrum data set corresponding to the partial area (patch) set in the step S1304 from a tentative spectrum data set. The tentative spectrum data is a set of #NpX*#NpY tentative spectra included in a patch. Next, the processing circuitry 51 outputs a static magnetic field deviation after deviation correction is performed and noise-reduced tentative spectrum data based on the tentative spectrum data, the configured machine learning model, and an estimated static magnetic field deviation. A static magnetic field deviation is, for example, the above-described $\Delta F$ value or a scaled $\Delta F$ value. By inputting the tentative spectrum data, the configured machine learning model, and the static magnetic field deviation, it can be expected that tentative spectrum data and a static magnetic field deviation having more accurate values than the input values can be output.

After step S1305, through the implementation of the reconstruction function 512, the processing circuitry 51 determines whether or not the moving of a partial area (patch) should be finished (step S1306). Step S1306 is similar to step S7.

When it is determined that the moving of the partial area should be terminated in step S1306 (Yes in step S1306), the processing circuitry 51 compensates errors in the tentative spectrum data set at the current number of iterations with respect to the acquired k-space data, through the implementation of the reconstruction function 512 (step S1307). Specifically, in step S1307, the processing circuitry 51 outputs an error-compensated tentative spectrum data set based on the noise-reduced tentative spectrum data and the acquired k-space data. Step S1307 is similar to step S1207.

After step S1307, through the implementation of the reconstruction function 512, the processing circuitry 51 determines whether or not the updating should be finished (step S1308). In step S1308, the processing circuitry 51 determines whether or not the predetermined condition for terminating updating is met. It suffices that the conditions for terminating updating are a condition that a predetermined number of updates has been fulfilled and a condition that an amount of updating a spectrum data set is less than a predetermined value, etc. If the conditions for terminating updating are not fulfilled, the processing circuitry 51 determines that the updating is not terminated and sets the partial area to an initial position and performs steps S1304 to S1308. The processing circuitry 51 repeats step S1304 through step S1308 until the condition for terminating updating is met. This repetition of step S1304 through step S1308 corresponds to the optimization process in which the noise reduction (step S1305) and the error compensation (step S1307) are repeated with the partial area being moved, until the condition for terminating updating is met.

The spectrum reconstruction including the repetition of steps S1306 to S1308 returns to the processing of minimizing an objective function, which is shown below as Expression (1). In the reconstruction processing shown in FIG. 13, F in Expression (1) represents the Fourier transform in both of a spatial direction and a temporal direction. S in Expression (1) represents a coil sensitivity to all spatial pixels and all frequencies, for example the same coil sensitivity to all frequencies. The coil sensitivity to all frequencies may not be strictly the same and the coil sensitivities may be different between frequencies. x in Expression (1) represents a spectrum for all spatial pixels and frequencies reconstructed with respect to both the spatial direction and the temporal direction. y in Expression (1) represents k-space data with respect to all k-space locations and all times that are not reconstructed with respect to both the spatial direction and the temporal direction.

If it is determined that the updating should be terminated in step S1308 (Yes in step S1308), the processing circuitry 51 completes the reconstruction through the implementation of the reconstruction function 512 (step S1309). In step S1309, the processing circuitry 51 outputs the spectrum data set at the stage of performing step S1309 as a reconstruction completed version. The spectrum data set of the reconstruction-completed version is stored in the memory 53. The processing circuitry 51 may extract a spectrum in a voxel of interest from the spectrum data set of the reconstruction completed version and display the spectrum on the display 55, or may reconstruct a molecular image showing a spatial distribution of a signal intensity value or a molecular weight of a molecule of interest based on a spectrum data set of the reconstruction completed version and display the molecular image on the display 55.

After step S1309, the reconstruction processing of the spectrum data set shown in FIG. 13 is finished.

According to the above example, the processing circuitry 51 to which spectrum data is input outputs noise-reduced spectrum data in the spectrum noise reduction. However, the processing circuitry 51 may output noise-reduced spectrum data upon input of spectrum data and system incomplete information. The system incomplete information is an estimated value that a $\Delta F$ value, which is a frequency deviation due to non-uniformity of a static magnetic field, can take. For example, the processing circuitry 51 first reduces an estimated value from the spectrum data then performs noise reduction on the spectrum data. Alternatively, the processing circuitry 51 performs noise reduction on the spectrum data and generates noise-reduced spectrum data, and then reduces an estimated value from the noise-reduced spectrum data. It is thereby possible to limit the frequency range of the spectrum to a predetermined range.

According to the above example, the partial area is a local area with respect to the spatial axis direction. However, the partial area may be a local area with respect to the time axis direction. For example, when data acquisition is performed multiple times on a plurality of voxels of a data acquisition period, spectrum data of the plurality of voxels of the data acquisition period is obtained as a spectrum data set. In this case, it suffices that the processing circuitry 51 sets a partial area in a local part within the data acquisition period. Thereafter, the processing circuitry 51 may perform the process of steps S4 to S10 on the set partial area. It is thus possible to reduce temporal non-uniformity in a static magnetic field by performing the process on a partial area that is set with respect to a time axis direction.

The present embodiment is applicable to retrospective sorting. Retrospective sorting is a method of sorting, after vital signals are acquired in parallel to non-gated data acquisition, time-series acquired raw data along a vital time phase, using the vital signals. The reconstruction is performed based on the sorted time-series acquired raw data. The signal intensity value I acquired with the retrospective sorting can be expressed in I(X, Y, Z, T, F0) as described earlier. At this time, the processing circuitry 51 may treat the signal intensity value I at time T1 and the signal intensity value I at time t2, which is in the same vital time phase as time T1 as the same value, and perform processing such as noise reduction and error compensation.

For example, if the retrospective sorting is performed based on an electrocardiograph signal, a signal intensity value of a heart beat phase where a first heart beat belongs and a signal intensity value of the heart beat phase of a second heart beat may be treated as the same. Furthermore, if the retrospective sorting is performed based on a respiratory signal, it suffices that a signal intensity value of a respiratory phase where a first breathing belongs and a signal intensity value of the respiratory phase of a second breathing are treated as the same value. Thus, the signal intensity value of a vital time phase of a vital cycle can be used in the same time phase of a different vital cycle; it is thereby possible to compensate a missing signal. Thus, it is possible to compensate a missing signal to perform noise reduction and error compensation in a unit of partial area.

The partial area may be set not only in either one of the spatial axis direction and the time axis direction but also in both the spatial axis direction and the time axis direction.

According to at least one embodiment described above, the accuracy in the reconstruction of a spectrum, etc. can be improved.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes its function by reading and executing the program stored in the storage circuitry. The program may be directly incorporated into the circuit of the processor instead of being stored in the storage circuit. In this case, the processor implements the function by reading and executing the program incorporated into the circuit. The function corresponding to the program may be implemented by a combination of logic circuits instead of executing the program. The processors described in connection with the above embodiments are not limited to single-circuit processors; a plurality of independent processors may be integrated into a single processor that implements the functions of the processors. Furthermore, a plurality of constituent elements shown in FIGS. 1 and 3 may be integrated into one processor to implement the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A reconstruction apparatus, comprising:
   processing circuitry configured to:
   obtain acquired raw data that is acquired by a medical image diagnosis apparatus; and
   reconstruct, based on the acquired raw data, a final data set that represents a measured physical quantity with a multi-dimensional space defined by a space axis, a time axis, and a component axis, wherein
   the processing circuitry is further configured to perform:
   reduction processing on first partial data relating to a partial area of an intermediate data set at a current number of iterations to generate noise-reduced second partial data;
   error compensation processing to compensate errors in the intermediate data set at the current number of iterations with respect to the acquired raw data; and
   optimization processing to reconstruct the final data set by repeating the reduction processing and the error compensation processing until predetermined criteria are met, while moving the partial area.

2. The reconstruction apparatus of claim 1, wherein
   in the reduction processing the processing circuitry is further configured to generate the second partial data by performing low-rank approximation on the first partial data.

3. The reconstruction apparatus of claim 2, wherein the processing circuitry is further configured to calculate a plurality of bases by performing matrix decomposition on the first partial data, select one or more bases that meet criteria relating to a contribution rate from the plurality of bases, and generate the second partial data by applying the one or more bases to the first partial data.

4. The reconstruction apparatus of claim 1, wherein
   in the reduction processing, the processing circuitry is further configured to generate the second partial data by applying a trained model to the first partial data, and
   the trained model is a machine learning model in which parameters are trained based on partial data for inputting including noise and partial data for teaching in which noise has been reduced.

5. The reconstruction apparatus of claim 4, wherein
   the acquired raw data is k-space data acquired through chemical shift imaging performed by a magnetic resonance imaging apparatus, and
   the final data set and the intermediate data set are each data of a spectrum representing a frequency distribution of a signal intensity value which is the measured physical quantity,
   the partial data for input is a pseudo spectrum obtained by applying a fluctuation function to a molecular spectrum model that includes a chemical shift frequency and a signal intensity value corresponding to the chemical shift frequency, the molecular spectrum model being shifted by a random frequency deviation amount, and
   the partial data for teaching includes the molecular model and the frequency deviation amount.

6. The reconstruction apparatus of claim 1, wherein in the error compensation processing, the processing circuitry is further configured to:
   obtain computed raw data from a synthesized data set obtained by synthesizing the second partial data and the intermediate data set at the current number of iterations, and
   update the intermediate data set at the current number of iterations based on errors between the computed raw data and the acquired raw data.

7. The reconstruction apparatus of claim 6, wherein
   the acquired raw data has first acquired raw data acquired by a first imaging method and second raw data acquired by a second imaging method, the processing circuitry is further configured to update the intermediate data set at the current number of iterations based on first errors between the computed raw data and the first acquired raw data and second errors between the computed raw data and the second acquired raw data.

8. The reconstruction apparatus of claim 1, wherein the processing circuitry is further configured to:
in the reduction processing, generate the second partial data based on the first partial data, a reference spectrum, and a static magnetic field deviation,
in the error compensation processing, compensate the errors in the intermediate data set at the current number of iterations based on the second partial data and the acquired raw data.

9. The reconstruction apparatus of claim 1, wherein the processing circuitry is further configured to:
in the reduction processing, generate the second partial data based on the first partial data, a machine leaning model, and a static magnetic field deviation,
in the error compensation processing, compensate the errors in the intermediate data set at the current number of iterations based on the second partial data and the acquired raw data.

10. The reconstruction apparatus of claim 1, wherein the processing circuitry is configured to perform the reduction processing on the first partial area relating to the partial area, which is a local area with respect to the space axis.

11. The reconstruction apparatus of claim 1, wherein the processing circuitry is configured to perform the reduction processing on the first partial area relating to the partial area, which is a local area with respect to the time axis.

12. The reconstruction apparatus of claim 1, wherein a size of the second partial data generated by the processing circuitry is smaller than a size of the first partial data.

13. The reconstruction apparatus of claim 1, wherein
the acquired raw data is k-space data acquired through chemical shift imaging performed by a magnetic resonance imaging apparatus, and
the final data set and the intermediate data set are each a spectrum representing a frequency distribution of a signal intensity value, which is the measured physical quantity, at each point in a temporary space defined by the space axis and the time axis in the multi-dimensional space.

14. A reconstruction method, comprising:
obtaining acquired raw data acquired by a medical image diagnosis apparatus; and
reconstructing, based on the acquired raw data, a final data set that represents a measured physical quantity with a multi-dimensional space defined by a space axis, a time axis, and a component axis, wherein
the reconstructing step further comprises performing:
reduction processing on first partial data relating to a partial area of an intermediate data set at a current number of iterations to generate noise-reduced second partial data:
error compensation processing for compensating errors in the intermediate data set at the current number of iterations with respect to the acquired raw data; and
optimization processing for reconstructing the final data set by repeating the reduction processing and the error compensation processing until predetermined criteria are met, while moving the partial area.

* * * * *